US010591628B2

(12) United States Patent
Fouda et al.

(10) Patent No.: US 10,591,628 B2
(45) Date of Patent: Mar. 17, 2020

(54) MULTIPURPOSE PERMANENT ELECTROMAGNETIC SENSING SYSTEM FOR MONITORING WELLBORE FLUIDS AND FORMATION FLUIDS

(71) Applicant: Halliburton Energy Services, Inc, Houston, TX (US)

(72) Inventors: Ahmed E. Fouda, Houston, TX (US); Tasneem Mandviwala, Katy, TX (US); Burkay Donderici, Houston, TX (US); Etienne Samson, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 63 days.

(21) Appl. No.: 15/125,650

(22) PCT Filed: Dec. 4, 2015

(86) PCT No.: PCT/US2015/064086
§ 371 (c)(1),
(2) Date: Sep. 13, 2016

(87) PCT Pub. No.: WO2017/095447
PCT Pub. Date: Jun. 8, 2017

(65) Prior Publication Data
US 2018/0017697 A1 Jan. 18, 2018

(51) Int. Cl.
*G01V 3/26* (2006.01)
*E21B 47/00* (2012.01)
(Continued)

(52) U.S. Cl.
CPC ............ *G01V 3/26* (2013.01); *E21B 47/0005* (2013.01); *E21B 47/123* (2013.01); *E21B 49/08* (2013.01);
(Continued)

(58) Field of Classification Search
CPC .... E21B 47/022; E21B 47/09; E21B 47/0905; E21B 47/02224; E21B 47/123;
(Continued)

(56) References Cited

U.S. PATENT DOCUMENTS 4,994,671 A 2/1991 Safinya et al.
6,053,245 A 4/2000 Haberman
(Continued)

FOREIGN PATENT DOCUMENTS

EP          0953726 A1    11/1999
WO  WO-2014109754 A1 *  7/2014  ....... E21B 47/02224
WO   WO 2014109754 A1 *  7/2014  ....... E21B 47/02224

OTHER PUBLICATIONS

International Search Report and The Written Opinion of the International Search Authority, or the Declaration, dated Sep. 2, 2016, PCT/US2015/064086, 9 pages, ISA/KR.

*Primary Examiner* — Douglas X Rodriguez
*Assistant Examiner* — Brent J Andrews
(74) *Attorney, Agent, or Firm* — Haynes and Boone, LLP

(57) ABSTRACT

Methods and systems of electromagnetic sensing in a wellbore are presented in this disclosure for monitoring annulus fluids and water floods. An array of transmitters and one or more receivers are located along a casing in the wellbore. A transmitter in the array and one of the receivers can be mounted on a same collar on the casing forming a transmitter-receiver pair. The receiver can receive a signal originating from the transmitter and at least one other signal originating from at least one other transmitter in the array, wherein the signal is indicative of a fluid in the wellbore in a vicinity of the transmitter-receiver pair and the at least one other signal is indicative of another fluid in a formation around the wellbore. The receiver can further communicate, via a waveguide, the signal and the at least one other signal to a processor for signal interpretation.

26 Claims, 13 Drawing Sheets

(51) Int. Cl.
*G01V 3/30* (2006.01)
*E21B 47/12* (2012.01)
*E21B 49/08* (2006.01)
*G01N 27/07* (2006.01)
*G01V 3/38* (2006.01)

(52) U.S. Cl.
CPC ............... *G01N 27/07* (2013.01); *G01V 3/30* (2013.01); *G01V 3/38* (2013.01); *E21B 2049/085* (2013.01); *Y02A 90/344* (2018.01)

(58) Field of Classification Search
CPC ..... E21B 49/08; E21B 47/0005; G01N 27/72; G01N 27/07; G01V 3/265; G01V 3/22; G01V 3/20; G01V 3/18; G01V 3/34; G01V 3/26; G01V 3/30; G01V 3/38
See application file for complete search history.

(56) References Cited

U.S. PATENT DOCUMENTS

| | | |
|---|---|---|
| 6,176,323 B1 | 1/2001 | Weirich et al. |
| 7,710,823 B2 | 5/2010 | Tabarovsky et al. |
| 8,505,625 B2 | 8/2013 | Ravi et al. |
| 2003/0058739 A1* | 3/2003 | Hsu ........................ G01V 1/284 367/56 |
| 2005/0093547 A1* | 5/2005 | Xiao ........................ G01V 3/28 324/339 |
| 2005/0194184 A1* | 9/2005 | Gleitman ............... E21B 17/028 175/45 |
| 2008/0068023 A1* | 3/2008 | Peter ........................ G01V 3/30 324/338 |
| 2012/0132007 A1 | 5/2012 | Dria et al. |
| 2012/0205103 A1 | 8/2012 | Ravi et al. |
| 2013/0239673 A1* | 9/2013 | Garcia-Osuna ......... E21B 17/16 73/152.46 |
| 2014/0151037 A1* | 6/2014 | Morgan-Smith ...... E21B 47/024 166/255.2 |
| 2014/0182848 A1* | 7/2014 | Roberson ................ E21B 33/13 166/253.1 |
| 2014/0191120 A1* | 7/2014 | Donderici ............. E21B 47/123 250/265 |
| 2014/0285204 A1* | 9/2014 | Okonkwo ............. E21B 47/011 324/333 |
| 2014/0338893 A1* | 11/2014 | Lively ................ E21B 17/1028 166/241.6 |
| 2015/0035536 A1 | 2/2015 | Tang |

* cited by examiner

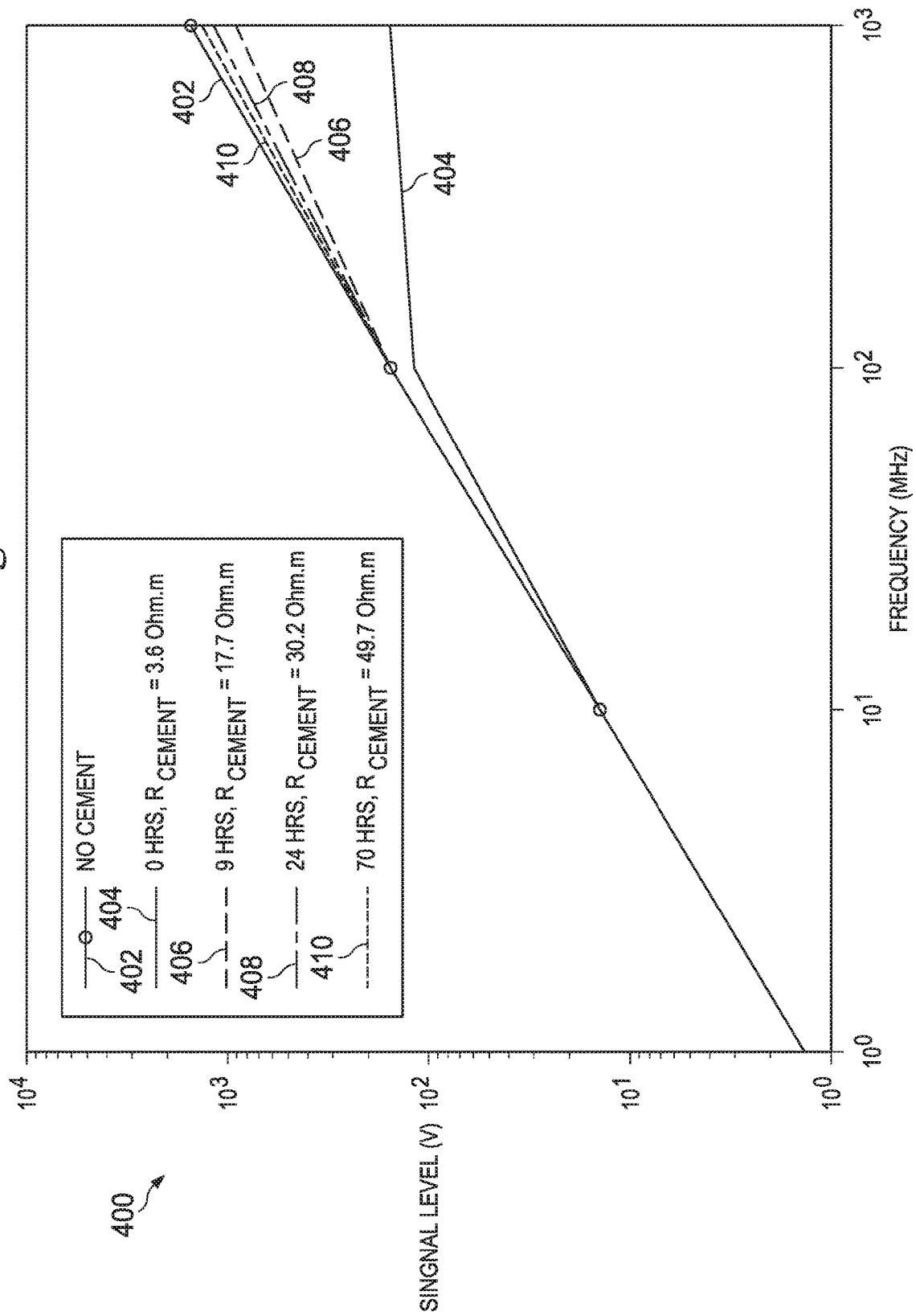

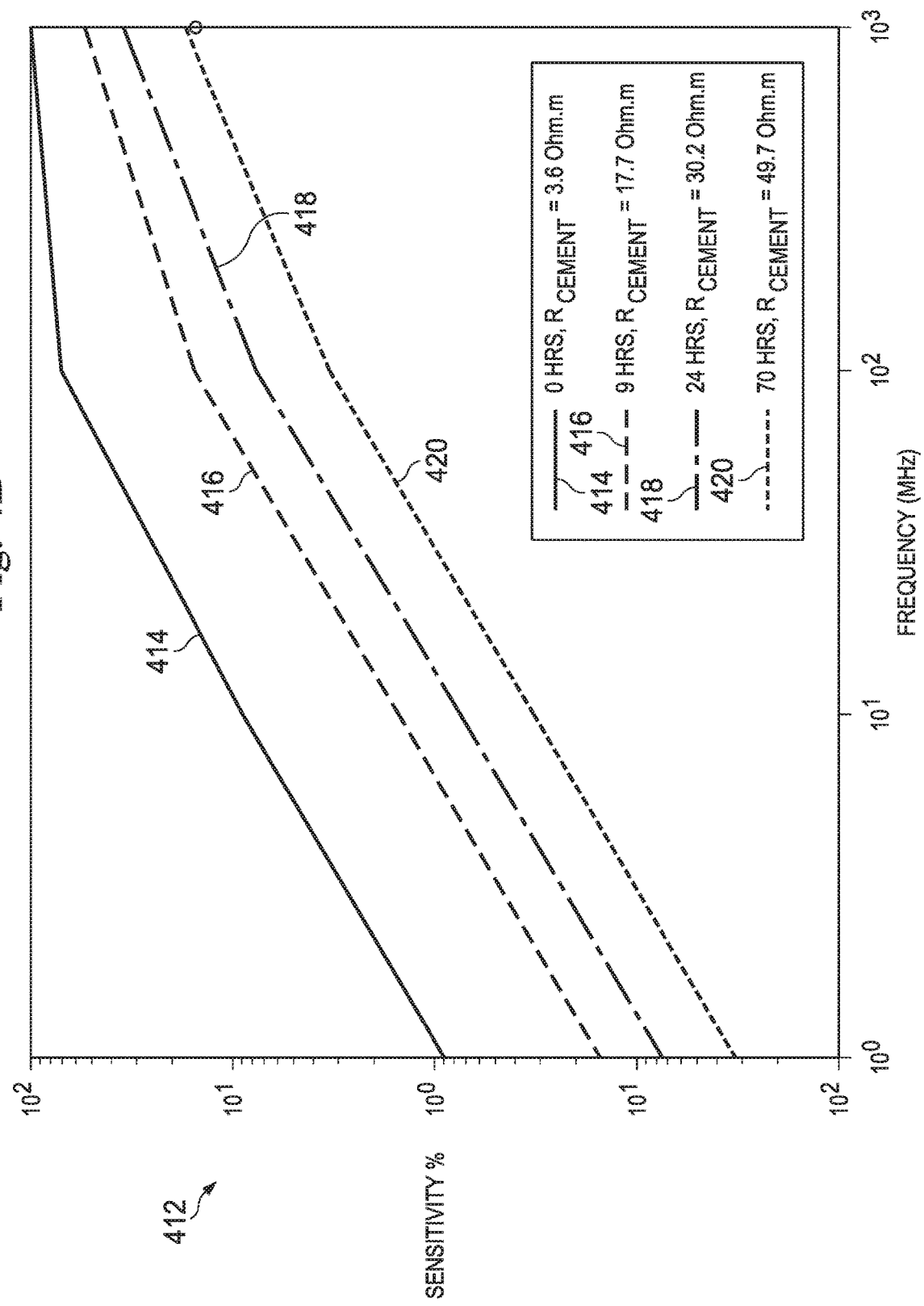

US 10,591,628 B2

MULTIPURPOSE PERMANENT ELECTROMAGNETIC SENSING SYSTEM FOR MONITORING WELLBORE FLUIDS AND FORMATION FLUIDS

PRIORITY

The present application is a U.S. National Stage patent application of International Patent Application No. PCT/US2015/064086, filed on Dec. 4, 2015, the benefit of which is claimed and the disclosure of which is incorporated herein by reference in its entirety.

TECHNICAL FIELD

The present disclosure generally relates to monitoring well completion operations and, more particularly, to a multi-purpose permanent electromagnetic sensing system for monitoring wellbore fluids and formation fluids during and after cementing operation.

BACKGROUND

During well completion, casing is emplaced in a wellbore. Drilling mud and/or spacer fluids are initially in place in an annulus region between casing and formation. As the cement slurry is pumped through the casing and into the annulus between the casing and the formation, the cement slurry displaces the spacer fluid, which in turn, displaces the drilling mud. The contamination of cement with drilling mud or spacer fluid can have significant negative consequences for the curing and integrity of the cement, and can provide potential conduits for flow behind casing.

Cement can be interrogated via various wireline-deployed through-casing resistivity (TCR) methods after the cement was emplaced in the annulus region between the casing and formation. However, the TCR methods have a number of deficiencies, such as significant signal attenuation through casing. Moreover, TCR methods require access to the well, and thus cannot be deployed in real-time as the cement slurry is being pumped into the well. Variety of distributed fiber optic sensing methods (e.g., based on monitoring acoustics, temperature, pressure, and the like) were also proposed for cement slurry monitoring. However, accuracy of these fiber optic sensing methods is often unsatisfactory.

Therefore, it is desirable to efficiently and accurately monitor the quality of cementation process during and after cement placement in the wellbore.

BRIEF DESCRIPTION OF THE DRAWINGS

Various embodiments of the present disclosure will be understood more fully from the detailed description given below and from the accompanying drawings of various embodiments of the disclosure. In the drawings, like reference numbers may indicate identical or functionally similar elements.

FIG. 4A is a graph illustrating a signal level at a receiver mounted on a casing collar as a function of receiving signal frequency before and after the cement placement in a wellbore, according to certain embodiments of the present disclosure.

FIG. 4B is a graph illustrating a percentage change in a signal level at a receiver mounted on a casing collar during the cement curing relative to no cement case in a wellbore, according to certain embodiments of the present disclosure.

DETAILED DESCRIPTION

Figure 1:
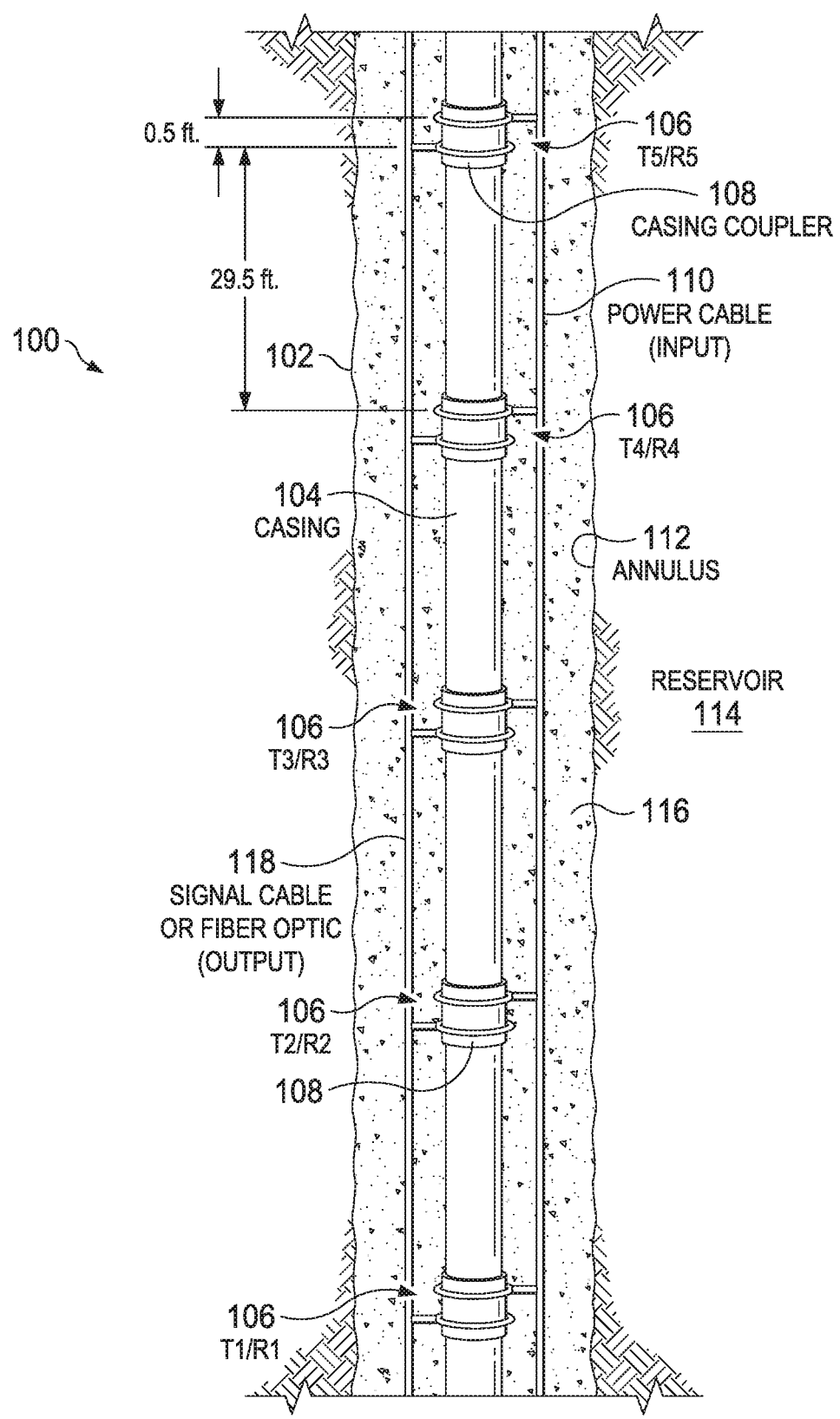
FIG. 1 is a cross-sectional view of an example of a well system that includes a magnetic field sensing system for wellbore resistivity measurements, according to certain embodiments of the present disclosure.

Embodiments of the present disclosure relate to a multi-purpose permanent electromagnetic sensing system for monitoring fluids in an annulus region in a wellbore between a casing and a formation during and after cement is emplaced in the annulus. The multi-purpose permanent electromagnetic sensing system presented in this disclosure can be also utilized for monitoring water floods from the formation into the wellbore. While the present disclosure is described herein with reference to illustrative embodiments for particular applications, it should be understood that embodiments are not limited thereto. Other embodiments are possible, and modifications can be made to the embodiments within the spirit and scope of the teachings herein and additional fields in which the embodiments would be of significant utility.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one ordinarily skilled in the art to implement such feature, structure, or characteristic in connection with other embodiments whether or not explicitly described. It would also be apparent to one ordinarily skilled in the relevant art that the embodiments, as described herein, can be implemented in many different embodiments of software, hardware, firmware, and/or the entities illustrated in the figures. Any actual software code with the specialized control of hardware to implement embodiments is not limiting of the detailed description. Thus, the operational behavior of embodiments will be described with the understanding that modifications and variations of the embodiments are possible, given the level of detail presented herein.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, uphole, downhole, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure, the uphole direction being toward the surface of the wellbore, the downhole direction being toward the toe of the wellbore. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Moreover even though a Figure may depict a horizontal wellbore or a vertical wellbore, unless indicated otherwise, it should be understood by those skilled in the art that the apparatus according to the present disclosure is equally well suited for use in wellbores having other orientations including vertical wellbores, slanted wellbores, multilateral wellbores or the like. Likewise, unless otherwise noted, even though a Figure may depict an offshore operation, it should be understood by those ordinarily skilled in the art that the apparatus according to the present disclosure is equally well suited for use in onshore operations and vice-versa. Further, unless otherwise noted, even though a Figure may depict a cased hole, it should be understood by those ordinarily skilled in the art that the apparatus according to the present disclosure is equally well suited for use in open hole operations.

Illustrative embodiments and related methods of the present disclosure are described below in reference to FIGS. 1-11 as they might be employed for monitoring fluids in an annulus region in a wellbore between a casing and a formation during and after cement is emplaced in the annulus, and for monitoring water floods from the formation into the wellbore. Such embodiments and related methods may be practiced, for example, using a computer system as described herein. Other features and advantages of the disclosed embodiments will be or will become apparent to one of ordinary skill in the art upon examination of the following figures and detailed description. It is intended that all such additional features and advantages be included within the scope of the disclosed embodiments. Further, the illustrated figures are only illustrative and are not intended to assert or imply any limitation with regard to the environment, architecture, design, or process in which different embodiments may be implemented.

Embodiments of the present disclosure generally relate to electromagnetic methods for monitoring an annulus formed between a formation and a casing in a wellbore. Embodiments of the present disclosure specifically relate to systems and methods for monitoring a top of cement, cement cure, mud cake, identifying annulus fluids (e.g., mud/spacer fluid/cement) and checking zonal isolation by monitoring cement integrity at each collar on a casing. In addition, the magnetic field sensing system presented herein comprising an array of transmitters and receivers located along the casing in the wellbore can be employed for monitoring water floods and other fluid flows from the formation into the wellbore.

For certain embodiments, in order to diagnose and assess quality of the cementation process during and after cement placement, as well as during the life-of-well (e.g., degradation due to $CO_2$ exposure), a plurality of electromagnetic sensor systems can be deployed azimuthally and/or axially on the casing in the wellbore with exposure to fluids in the annulus between the casing and formation. The deployed electromagnetic sensor systems can be configured to transmit, receive, process, and telemeter electromagnetic signals to a central processing unit located, for example, at a well head. In relation to that, a method for focused impedance analysis for fluid discrimination and monitoring in a wellbore may be utilized. Furthermore, a method for monitoring wellbore cement using electric current injected from the casing may be applied along with permanent electric field sensors. In addition, methods for detecting and/or monitoring the position and/or condition of wellbore compositions, for example wellbore sealants such as cement, using fluid sensing components and Radio Frequency Identification (RFID) tags, in some cases including Micro-Electro-Mechanical System (MEMS) based data sensors, for sensing properties of fluids may be employed.

In relation to embodiments of the present disclosure, an electromagnetic monitoring system may be deployed downhole to monitor approaching waterflood in enhanced oil recovery environments. Furthermore, certain related embodiments encompass systems and methods of acquiring, processing, and imaging electromagnetic data acquired from an electromagnetic system with electromagnetic sensors deployed behind casing in a wellbore.

Embodiments of the present disclosure relate to systems and methods for implementing an array of magnetic field transmitters and receivers configured to perform time-lapse measurements for identifying annulus fluids in a wellbore. Further, some embodiments of the present disclosure utilize the presented array of magnetic field transmitters and receivers for determining fluid flows in a formation around the wellbore. As discussed in more detail below, a fluid in the annulus formed in the wellbore between the casing and formation (e.g., mud/cement/spacer) and a fluid in the formation can be characterized and identified based on their resistivities. Some embodiments of the present disclosure relate to shallow resistivity measurements in the annulus. In addition, as the cement cure progresses, the resistivity increases over time until the cement is fully cured. In accordance with embodiments of the present disclosure, the change in cement resistivity over time can be monitored using time-lapse magnetic field measurements. In one or more embodiments, the measured magnetic field (i.e., measured signal levels) can be converted into resistivity indication through specific inversion algorithm(s). Then, the obtained resistivity indication can be correlated to a type of fluid present in the annulus between the casing and formation. Further, resistivity indication related to magnetic field measurements in the formation can be correlated to a type of fluid present in the formation around the wellbore.

For certain embodiments, as discussed in more detail below, RFID tags may be mixed with cement as it is being pumped into a wellbore (e.g., into an annulus formed between a casing and formation), and an array of magnetic field transmitters and receivers may be employed to interrogate the RFID tags in the cement in order to detect curing state of cement, a top of cement, and the like. The top of cement defines the interface between the cement and other annulus fluids. In a preferred embodiment, the top of cement is a flat, piston-like displacement. However, more often, the top of cement is more complex with certain fluids (e.g., drilling mud or spacer fluid) not flushing properly and degrading cement quality and well integrity. As discussed in more detail below, the method of detecting the top of cement can be applied for monitoring the progression of cement in the annulus and for detecting any discontinuities in the cement due to improperly displaced annulus fluids.

The electromagnetic sensing system presented in this disclosure can be configured to communicate obtained measurements to, for example, an uphole central processing unit using waveguides interfaced with the sensing system. Thus, active electronic components may be deployed downhole for signal digitalization. Embodiments of the present disclosure relate to an array of magnetic field transmitters and receivers located axially or azimuthally along a casing in a wellbore configured for monitoring annulus fluids. Furthermore, the array of magnetic field transmitters and receivers can be also utilized to perform deep measurements for reservoir monitoring as well as for waterflood detection. Thus, the permanently deployed electromagnetic sensing system presented in this disclosure can be employed for both reservoir monitoring (e.g., deep measurements) and wellbore (annulus) fluids monitoring (e.g., shallow measurements). In addition, as discussed in more detail below, the electromagnetic sensing system presented herein can be utilized for both wellbore (annulus) fluids resistivity measurements and for RFID tags interrogation. In one or more embodiments, measured signals can be communicated uphole using fiber optic based methods, wherein active electronic components and circuits can be deployed downhole.

The electromagnetic sensing system presented in this disclosure does not require any downhole electrical power consumption. In addition, the electromagnetic sensing system presented herein can be integrated and operable along with other fiber optic based sensing systems (e.g., distributed acoustic sensing, distributed temperature sensing, etc.). Furthermore, the presented electromagnetic sensing system can be integrated with intelligent well completion methods for monitoring wellbore (annulus) cement. Moreover, embodiments of the present disclosure relate to monitoring annulus fluids to facilitate future water flood estimations and predictions (e.g., water floods from formation to a wellbore), because the fluid monitoring results can be utilized for calibrating measured signals to a particular water flood model.

Embodiments of the present disclosure relate to time lapse measurements of fluid resistivity, which can be accomplished by measuring magnetic fields, as discussed in more detail below. For certain embodiments, transmitters of the electromagnetic sensing system presented herein can be configured as an array of coils mounted on a steel casing, connected in series and fed by an electric power cable. In one or more embodiments, another array of magnetic field receivers (array of coils) can be mounted on the casing, wherein a transmitter-receiver pair may be mounted (e.g., co-located) on the same casing collar (e.g., a transmitter and a receiver of the transmitter-receiver pair may be 0.5 ft. or less apart).

FIG. 1 is a cross-sectional view 100 of an example of a well system that includes a magnetic field sensing system configured for performing wellbore resistivity measurements, according to certain illustrative embodiments of the present disclosure. A wellbore 102 contains a casing 104 with an array of magnetic field transmitters and receivers 106 mounted on the casing 104. As illustrated in FIG. 1, the transmitters 106 may be configured as an array of coils mounted on collars (e.g., casing couplers) 108 of the casing 104, and the receivers 106 may be configured as an array of coils mounted on the same casing collars 108. For example, as further illustrated in FIG. 1, a transmitter and a receiver of transmitter/receiver pair 106 mounted on the same casing collar 108 may be placed (co-located) approximately 0.5 ft. or less apart, whereas adjacent transmitter/receiver pairs 106 mounted on different casing collars 108 may be, for example, approximately 29.5 ft. apart.

For certain embodiments, as illustrated in FIG. 1, the transmitters 106 mounted on the casing 104 may be connected in series and fed by an electric power cable 110, with a power generator (not shown) interfaced to the electric power cable 110 generating signals for the transmitters 106 having a pre-determined range of frequencies. An annulus 112 formed between the casing 104 and reservoir formation 114 may be filled with cement 116 in order to secure the casing 104 in place and prevent fluid flows in the annulus 112. In one or more embodiments, a fluid (e.g., a hydrocarbon such as oil or gas) may enter the uncemented portion of the well (or alternatively, a fluid may enter through perforated portions of the well casing) and reaches the surface (not shown) through the interior of the casing 104.

It should be noted that this particular well configuration is merely illustrative and not limiting on the scope of the disclosure. Many production wells are provided with multiple production zones that can be individually controlled. Similarly, many injection wells are provided with multiple injection zones that can be individually controlled. In one or more embodiments, signals may be induces into the cement 116 and/or formation 114 through the magnetic field transmitters 106 that emulate a magnetic field source. The array of magnetic field receivers 106 deployed on the same collars 108 as the transmitters 106 may receive output signals or measurements related to the state of cement 116 and/or formation 114. The measurements received by the receivers 106 may be then communicated to a surface interface or a computer system for further processing (not shown) via output signal cable 118 connected to the receivers 106. In one or more embodiments, the output signal cable 118 may be a low transmission loss waveguide. An electromagnetic signal received at each receivers 106 may be encoded (e.g., by circuitry coupled to each receiver 106) into the low transmission loss waveguide connected to the receivers 106. The waveguide may transmit the electromagnetic signal(s) from at least one of the receivers 106 to the surface interface or the computer system for signal decoding and signal interpretation. In an embodiment of the present disclosure, the waveguide may be a fiber optic cable (e.g., cable 118 in FIG. 1) connected to the receivers 106.

For certain embodiments, the surface interface may be coupled to a computer that acts as a data acquisition system and possibly as a data processing system that analyzes the measurements to derive subsurface parameters and track the location of a fluid front. In one or more embodiments, the computer may further control production parameters to reduce risk of break-through or to otherwise optimize production based on the information derived from the measurements. Production parameters may include the flow rate/pressure permitted from selected production zones, flow rate/pressure in selected injection zones, and the composition of the injection fluid, each of which can be controlled via computer controlled valves and pumps.

Generally, any such computer would be equipped with a user interface that enables a user to interact with the software via input devices such as keyboards, pointer devices, and touchscreens, and via output devices such as printers, monitors, and touchscreens. The software can reside in computer memory and on non-transient information storage media. The computer may be implemented in different forms including, e.g., an embedded computer permanently installed as part of the surface interface, a portable computer that is plugged into the surface interface as desired to collect data, a remote desktop computer coupled to the surface interface via a wireless link and/or a wired computer network, a mobile phone/personal digital assistant (PDA), or any electronic device having a programmable processor and an interface for input/output (I/O).

In one or more embodiments, the measurements received by the receivers 106 may be communicated (e.g., via waveguide 118) to a downhole processor (not shown). The downhole processor may be configured to process the measurements provided by the receivers 106 and to communicate, using waveguide 118, processed information to a surface interface or a surface computer system for possible further analysis and processing (not shown). This configuration may be advantageous because there may be a smaller amount of data for transferring to the surface computer system after processing the measurements by the downhole processor in comparison with direct communication of the measurements from the receiver 106 to the surface computer system.

Figure 2:
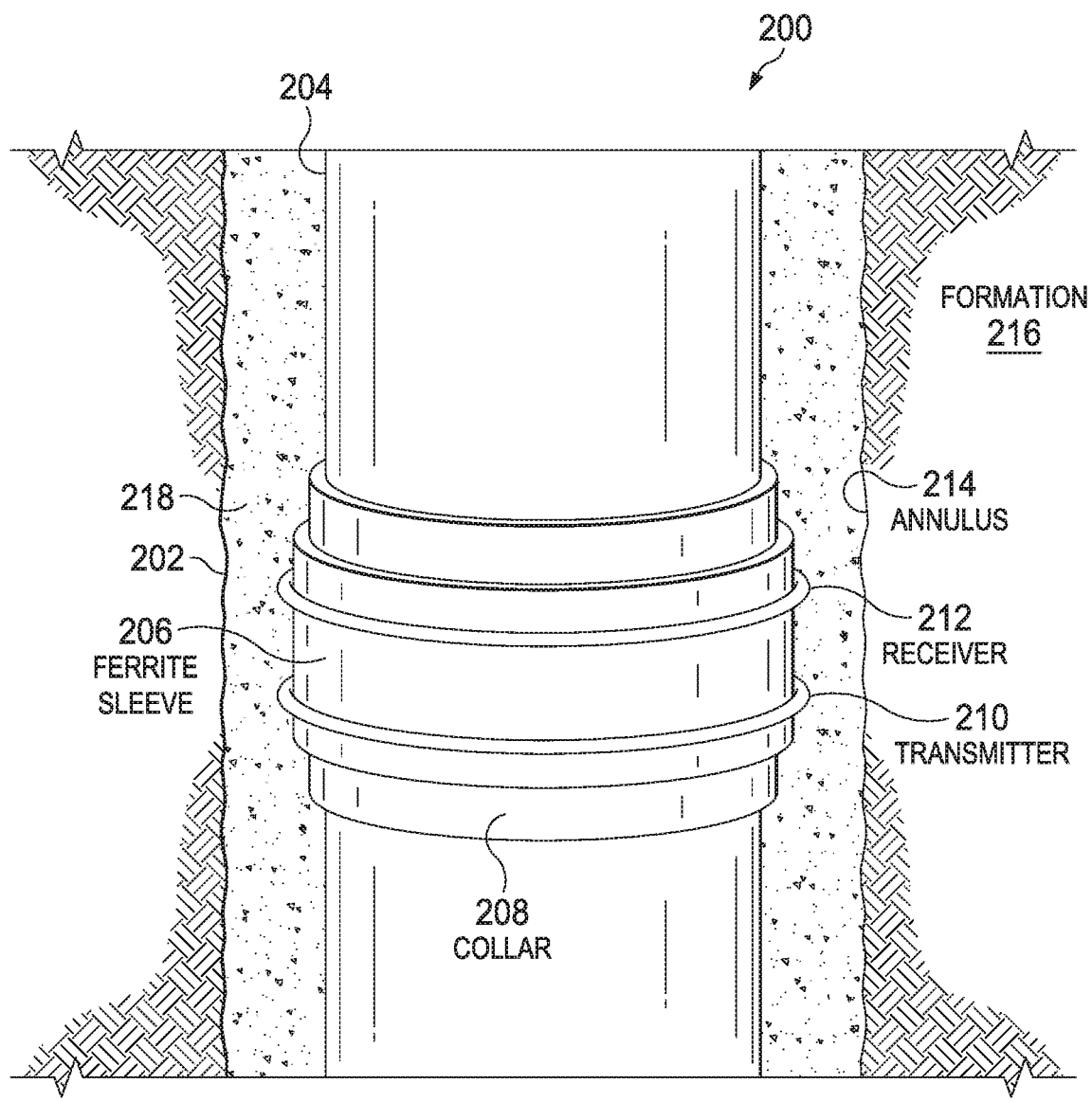
FIG. 2 is a cross-sectional view of an example transmitter and receiver mounted on the same collar on a casing in a wellbore, according to certain embodiments of the present disclosure.

FIG. 2 is a cross-sectional view 200 of an example transmitter and receiver (e.g., transmitter/receiver pair 106 illustrated in FIG. 1) mounted on the same collar on a casing deployed in a wellbore, according to certain illustrative embodiments of the present disclosure. A wellbore 202 may contain a casing 204 having a ferrite sleeve 206 positioned on a collar 208. As illustrated in FIG. 2, a magnetic field transmitter 210 and a magnetic field receiver 212 (which may correspond to transmitter/receiver pair 106 illustrated in FIG. 1) may be coils mounted on the same ferrite sleeve 206 on the same collar 208. An annulus 214 formed between the casing 204 and formation 216 may be filled with cement 218 in order to secure the casing 204 in place and prevent fluid flows in the annulus 214.

Referring back to FIG. 1, for certain embodiments, the magnetic field sensing system comprising the array of transmitter/receiver pairs 106 mounted on casing collars 108 may be applied to improve a dynamic range of magnetic field measurements for reservoir monitoring. In one or more embodiments, odd and even (e.g., consecutive) transmitters 106 may be fed by separate power cables that are independently controlled. In order to perform reservoir monitoring measurements (e.g., deep measurements) at even receivers 106, odd transmitters 106 are energized with a high-level current, whereas even transmitters 106 are energized with a low-level current with opposite phase, so as to cancel out (buck) direct signals at even receivers 106. The alternate approach can be applied to perform measurements at odd receivers 106. For some embodiments related to reservoir monitoring, signals having the frequency range between 1 kHz and 100 kHz may be used. For embodiments related to wellbore (annulus) fluids monitoring, all transmitters 106 can be energized simultaneously and measurements can be performed at adjacent (e.g., co-located) receivers 106 mounted on the same casing collar 108. Signals having the frequency range of 1 MHz to several GHz may be used for wellbore (annulus) fluids monitoring.

In one or more embodiments, the magnetic field sensing system (e.g., the array of transmitters and receivers 106 mounted on casing collars illustrated in FIG. 1) may comprise a magnetostrictive material bonded to a waveguide (e.g., signal cable 118 in FIG. 1). Examples of magnetostrictive materials include, but are not limited to, cobalt, nickel, and iron metals and their alloys, such as metglass and Terfenol-D. As the magnetostrictive material deforms due to the incident magnetic field, the magnetostrictive material may induce strain in the waveguide bonded to the material. In one or more embodiments, the strain may be interrogated at the surface using certain multiplexing and interrogation techniques, which may require deployment of multiplexing circuitry downhole. The system can be operated such that the strain is linearly proportional to the applied field.

In one or more embodiments, magnetic field sensors can be packaged in electromagnetic compatible high pressure, high temperature packages that are connected to a tubing encapsulated cable (TEC), and clamped to the casing as the casing is being deployed into the wellbore. Signals from other receivers (e.g., at different axial locations) can be communicated over the same TEC cable to, for example, a surface interface coupled to a computer acting as a data acquisition system. For certain embodiments, the signals from different receivers may be discriminated at the surface interface and/or the coupled computer using, for example, certain multiplexing and interrogation techniques.

In one or more other embodiments, pick-up coils (e.g., coils of transmitters/receivers 106 illustrated in FIG. 1, coils of transmitter 210 and receiver 212 illustrated in FIG. 2) can be used to convert a magnetic field into a potential difference (voltage) applied to an electro-mechanical transducer (not shown). As the electro-mechanical transducer deforms due to the applied potential difference (voltage), the transducer induces strain in a waveguide (e.g., the signal cable 118 illustrated in FIG. 1) bonded to the transducer. In one or more other embodiments, an electronic switching circuit (not shown) can be used to multiplex signals from different magnetic field sensors (e.g., pick-up coils illustrated in FIGS. 1 and 2) to an electric cable or a waveguide (e.g., the electric power cable 110 in FIG. 1, or the signal cable 118 in FIG. 1) that delivers the signal uphole. In an embodiment, casing centralizers (not shown) can be employed to preserve spacing between the casing 104 and the wellbore 102, and therefore protects the receivers (sensors) 106 from damage as the casing 104 is deployed downhole.

For certain embodiments of the present disclosure, the array of magnetic field transmitter-receiver pairs 106 illustrated in FIG. 1 may be a part of a dual-purpose electromagnetic sensing tool (e.g., logging tool) deployed in the wellbore 102 and configured for monitoring wellbore fluids and formation fluids. In this case, the array of transmitter-receiver pairs 106 of the logging tool may be adapted to be located along the casing 104 in the wellbore 102. Each receiver (e.g., the receiver 106 in FIG. 1, the receiver 212 in FIG. 2) of a transmitter-receiver pair (e.g., the transmitter-receiver pair 106 in FIG. 1, the transmitter-receiver pair 210-212 in FIG. 2) may be further adapted to receive a signal originating from a transmitter (e.g., the transmitter 106 in FIG. 1, the transmitter 210 in FIG. 2) of the transmitter-receiver pair and at least one other signal originating from at least one other transmitter (e.g., other transmitters 106 in FIG. 1) in the array. In one or more embodiments, the signal received at that receiver of the logging tool may be indicative of a fluid (e.g., resistivity of a fluid) in the wellbore 102 in a vicinity of the transmitter-receiver pair, and the at least one other signal received at that receiver of the logging tool may be indicative of a fluid (e.g., resistivity of a fluid) in the formation 114 around the wellbore 102.

Monitoring Cement Cure State

Figure 3:
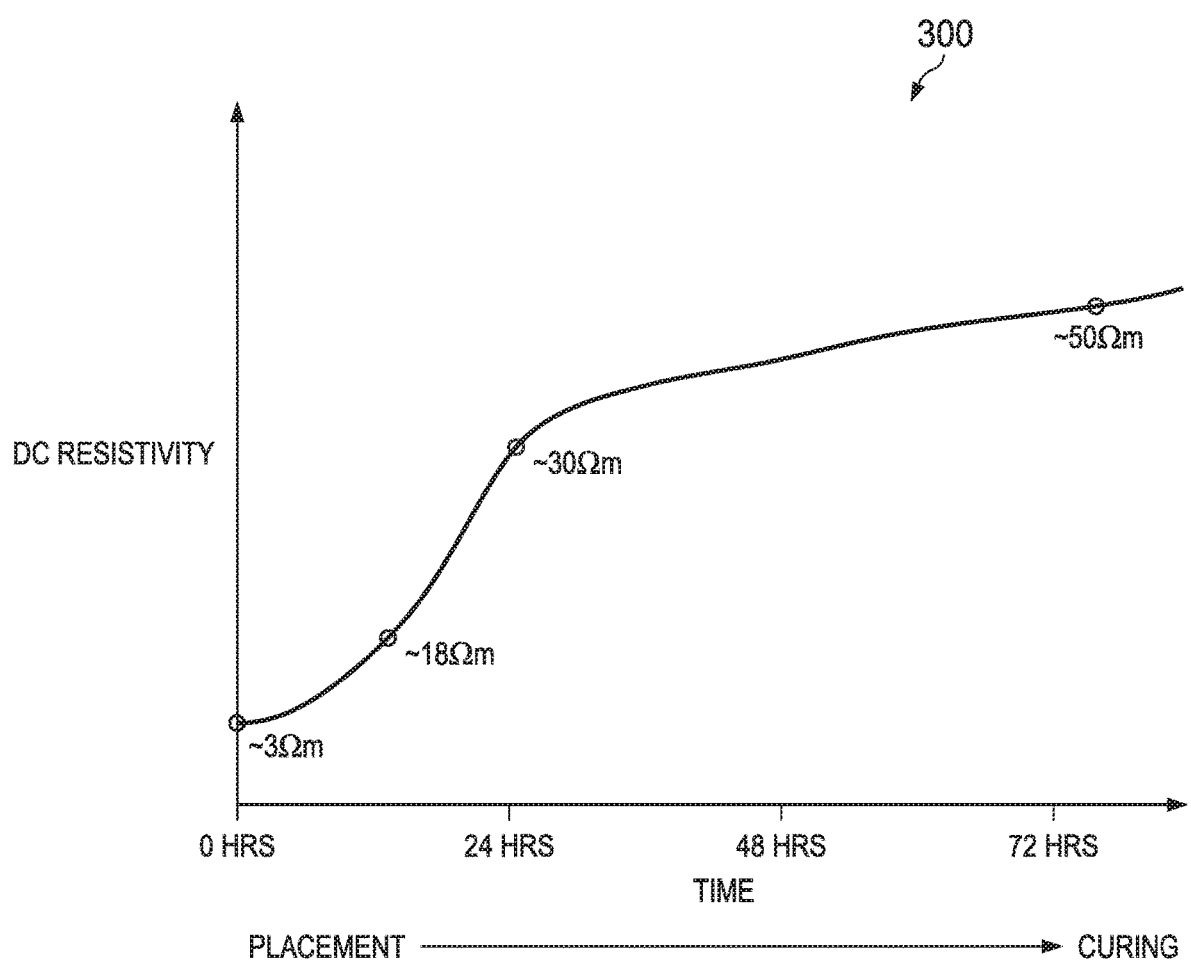
FIG. 3 is a graph illustrating a conceptual model of cement resistivity varying from placement to curing, according to certain embodiments of the present disclosure.

FIG. 3 is a graph 300 illustrating a conceptual model of cement DC resistivity varying over time from placement to curing, according to certain illustrative embodiments of the present disclosure. It can be observed from FIG. 3 that, during the cement curing process, the resistivity of the cement gradually increases. Hence, in one or more embodiments of the present disclosure, monitoring the resistivity of cement over time may provide essential information on the cement curing process. Embodiments of the present disclosure relate to a method and apparatus for monitoring the cement cure state through monitoring the cement resistivity via time-lapse magnetic field measurements.

Referring back to FIG. 1, in the time-lapse magnetic field measurement system, a receiving signal may be recorded at each receiver 106 along the casing 104 at an initial time before the cement is pumped into the annulus 112. This initial receiver signal can be referred to as the baseline signal. After the cement 116 is pumped into the annulus 112 and as the cement cures, a signal at each receiver 106 may be recorded and the baseline signal may be subtracted off the newly recorded signal. In one or more embodiments, a level of the obtained differential signal may be a function of the resistivity of cement. Thus, time-lapse processing of the differential signals obtained at the receivers 106 along the casing 104 may provide an indication on how cement curing has been progressing. In an embodiment, the baseline signal may be utilized to calibrate the transmitter/receiver sensing system illustrated in FIG. 1 given the wellbore size from the caliper log and the electric resistivity of the annulus fluids (e.g., mud and/or spacer fluid) before pumping the cement.

In an illustrative embodiment, the magnetic sensing system comprising the array of transmitters/receivers 106 illustrated in FIG. 1 can be deployed in a 9" wellbore (e.g., wellbore 102 in FIG. 1). The cement 116 can be pumped in so that the annulus 112 between the casing 104 and the formation 114 is filled with the cement. In this illustrative embodiment, the cement resistivity varies from approximately 3 Ωm to approximately 50 Ωm over approximately 72 hours of curing time. The formation resistivity is known and equal to approximately 100 Ωm, which provides resistivity contrast between the cement 116 and the formation 114. Before pumping the cement, the wellbore 102 may be filled with oil-based mud having resistivity of approximately 100 Ωm, which also provides resistivity contrast to the cement 116 pumped into the annulus 112.

Using the cement resistivity values as a function of curing time, a numerical model can be constructed to study the magnetic field sensitivity of the magnetic sensing system comprising the array of transmitters/receivers 106 illustrated in FIG. 1. The numerical model comprises 7" diameter steel casing (e.g., the casing 104 illustrated in FIG. 1), having relative permeability of 100 and conductivity of 107 S/m. The transmitter-receiver pair 106 mounted on the same collar 108 on the casing 104 (or the transmitter 210 and the receiver 212 illustrated in FIG. 2) can be made of singe turn coils of diameter 8", and spaced 6" apart. The ferrite sleeve under the coils (e.g., the ferrite sleeve 206 illustrated in FIG. 2) can be 0.45" thick, 10" in length having relative permeability of 250. An electric current equal to 1 A can be injected into the transmitter (e.g., the transmitter 106 in FIG. 1, the transmitter 210 in FIG. 2).

FIG. 4A is a graph 400 illustrating a signal level at a receiver mounted on a casing collar (e.g., the receiver 106 illustrated in FIG. 1, the receiver 212 illustrated in FIG. 2) as a function of receiving signal frequency (e.g., MHz range for shallow measurements of annulus fluids) before and after the cement placement in the annulus, according to certain illustrative embodiments of the present disclosure. Plot 402 in FIG. 4A illustrates the signal level at the receiver as a function of signal frequency when there is no cement in the annulus; plot 404 in FIG. 4A illustrates the signal level at the receiver as a function of signal frequency when the cement is just emplaced in the annulus; plot 406 in FIG. 4A illustrates the signal level at the receiver as a function of signal frequency when the cement in the annulus is cured for about 9 hours; plot 408 in FIG. 4A illustrates the signal level at the receiver as a function of signal frequency when the cement in the annulus is cured for about 24 hours; and plot 410 in FIG. 4A illustrates the signal level at the receiver as a function of signal frequency when the cement in the annulus is fully cured (e.g., approximately 70 hours after being emplaced in the annulus). It can be observed from FIG. 4A, as the more conductive wet cement displaces the more resistive wellbore (annulus) fluid (e.g., drilling mud), signal levels at receivers and collars embedded in the cement drop (e.g., plot 404 shows signal levels at the receiver for different signal frequencies when the cement is just emplaced in the annulus). As the cement in the annulus cures, the cement becomes less conductive and the signal level at the receiver increases approaching the no cement case, as illustrated by plots 406, 408 and 410 in FIG. 4A.

FIG. 4B is a graph 412 illustrating a percentage change in a signal level at a receiver (e.g., the receiver 106 illustrated in FIG. 1, the receiver 212 illustrated in FIG. 2) mounted on a casing collar as a function of receiving signal frequency during the cement curing relative to no cement case in a wellbore, according to certain illustrative embodiments of the present disclosure. It can be observed from FIG. 4B that the change in the signal level is the largest immediately after the cement is emplaced in the annulus (e.g., plot 414 in FIG. 4B), and that the change in the signal level relative to no cement case decreases as the cement cures (e.g., plots 416, 418 and 420 in FIG. 4B corresponding to the cases when the cement is cured for about 9 hours, 24 hours and 70 hours, respectively). It can be also observed from FIG. 4B that the sensitivity (e.g., change in the signal level at the receiver) increases with a frequency of receiving signal. In one or more embodiments, the signal sensitivity is at a highest level for a certain preferred frequency (not shown), beyond which it begins to drop.

Monitoring Annulus Fluids

During well completion, a casing is emplaced in a wellbore. Drilling mud and/or spacer fluids are initially in place in an annulus region formed between the casing and formation. As the cement slurry is pumped through the casing and into the annulus between the casing and formation, the cement slurry displaces the spacer fluid, which in turn, displaces the drilling mud. The contamination of cement with drilling mud and/or spacer can have significantly negative consequences for the curing and integrity of the cement, and can provide potential conduits for flow behind the casing.

Figure 5:
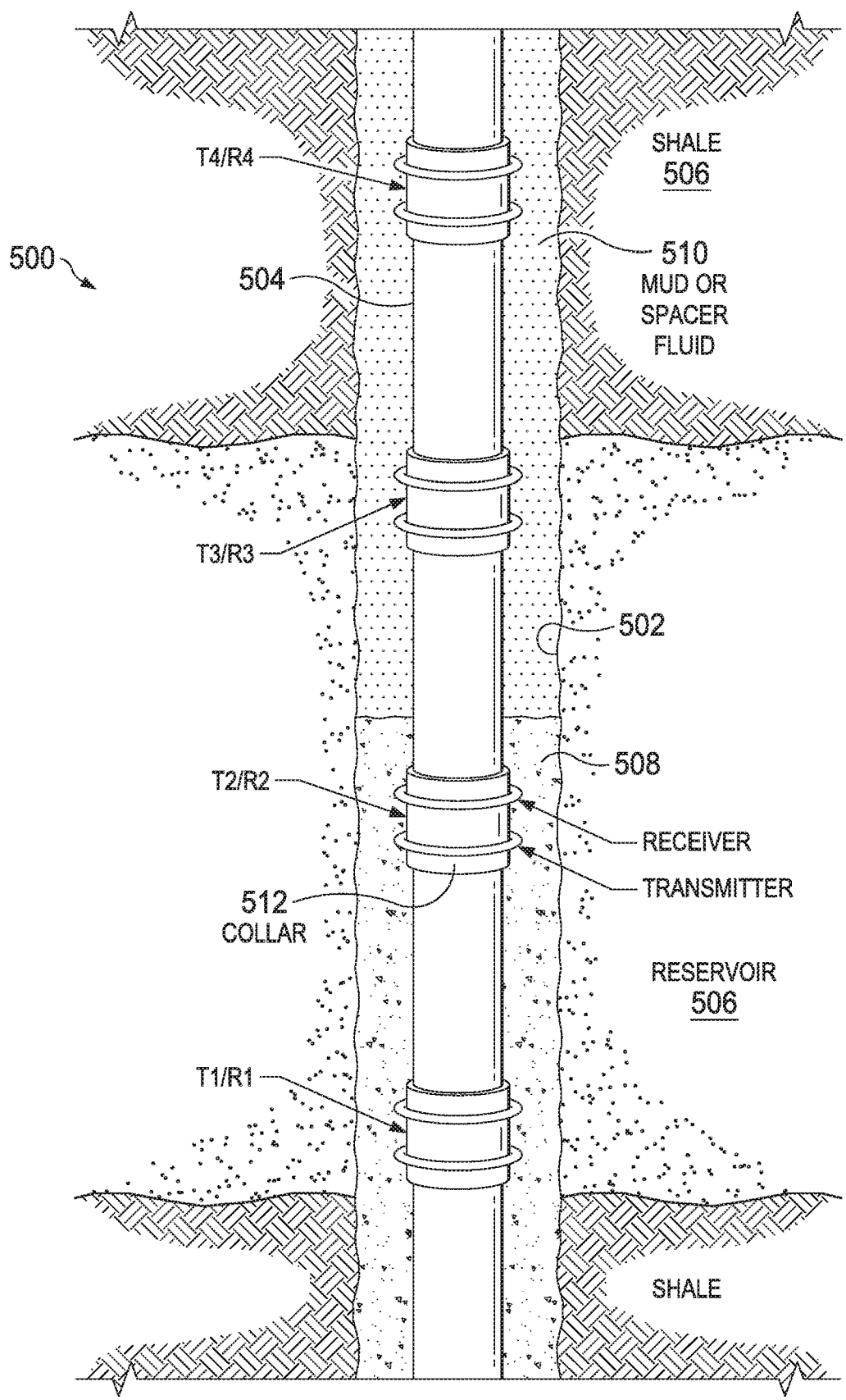
FIG. 5 is a cross-sectional view of an example of a well system that includes a magnetic field sensing system for monitoring and identifying annulus fluids in a wellbore, according to certain embodiments of the present disclosure.

FIG. 5 is a cross-sectional view 500 of an example of a well system that includes a magnetic field sensing system (e.g., an array of transmitters/receivers mounted on casing collars) for monitoring and identifying annulus fluids, according to certain illustrative embodiments of the present disclosure. As illustrated in FIG. 5, an annulus 502 formed between a casing 504 and a formation 506 (e.g., shale or reservoir formation) may be filled with cement 508 and some other fluid 510 (e.g., an oil-based mud or a spacer fluid). The cement resistivity may vary from approximately 3 Ωm to approximately 50 Ωm over approximately 72 hours of cement curing time. On the other hand, the oil-based mud is more resistive than the cement, hence providing the resistivity contrast. By employing the magnetic field sensing system illustrated in FIG. 1 and illustrated again in FIG. 5 comprising the array of transmitters/receivers (i.e., array of coils) mounted on casing collars 512, the time lapse resistivity measurements of annulus fluids can be achieved. Thus, in accordance with certain embodiments of the present disclosure, the magnetic field sensing systems illustrated in FIGS. 1 and 5 may provide the ability to characterize fluids in the annulus region in the wellbore between the casing and formation over the life of well.

Figure 6:
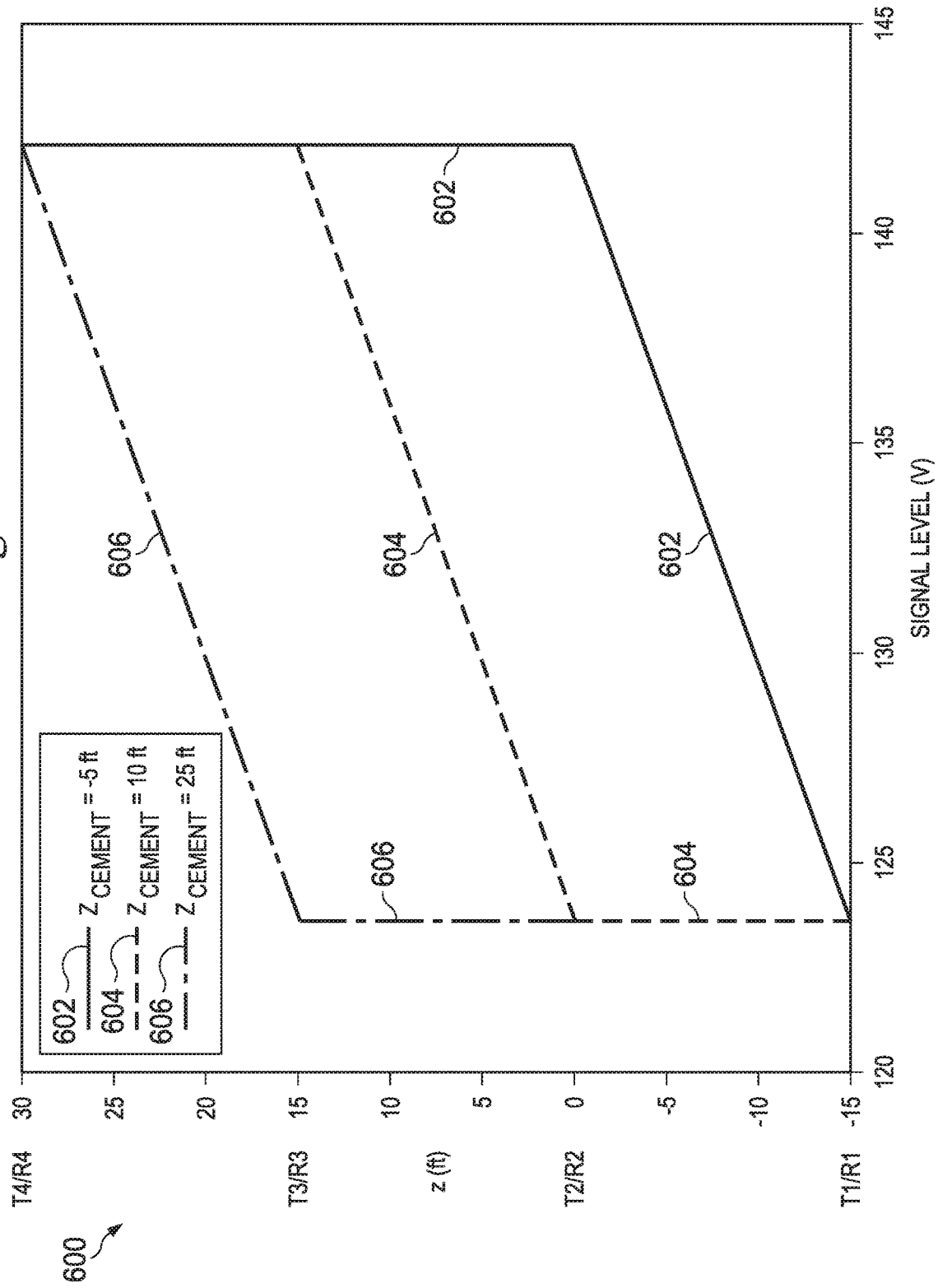
FIG. 6 is a graph illustrating signal levels at different receivers along a casing in a wellbore for different locations of a top of cement in an annulus between the casing and formation, according to certain embodiments of the present disclosure.

An illustrative example of signal levels obtained at the receivers of the magnetic field sensing system illustrated in FIG. 5, operating at 100 MHz, is shown in FIG. 6. FIG. 6 is a graph 600 illustrating signal levels at different receivers along the casing 504 for different locations of a top of the cement 508 in the annulus 502, according to certain illustrative embodiments of the present disclosure. It can be observed from plot 602 in FIG. 6 that, if the top of cement in the annulus 502 is at −5 ft., signal levels at the receivers R4, R3, R2 positioned above the top of cement are high due to a high resistivity of oil-based mud located in that section of the annulus 502, whereas the signal level at the receiver R1 is low since this receiver is positioned below the top of cement in the annulus 502. When the top of cement in the annulus 502 reaches 10 ft., signal levels at the receivers R4, R3 positioned above the top of cement are still high due to a high resistivity of oil-based mud still located in that section of the annulus 502, whereas the signal levels at the receivers R1, R2 are low since these two receivers are now positioned below the top of cement in the annulus 502, as illustrated by plot 604 in FIG. 6. When the top of cement in the annulus 502 reaches 25 ft., only signal level at the receiver R4 positioned above the top of cement is still high due to a high resistivity of oil-based mud still located around the receiver R4 in the annulus 502, whereas the signal levels at all other receivers R1, R2, R3 are low since receivers R1, R2, R3 are now positioned below the top of cement in the annulus 502, as illustrated by plot 606 in FIG. 6. Thus, signal level profile at different receivers can be sensitive to the resistivity of the wellbore (annulus) fluid adjacent to each receiver. As illustrated in FIG. 6, signal levels at casing collars embedded in cement drop as the more conductive cement displaces the more resistive wellbore (annulus) fluid (e.g., drilling mud). Therefore, the magnetic field sensing systems illustrated in FIGS. 1 and 5 can be efficiently employed to estimate the top of cement in the annulus and the annulus fluid composition.

Monitoring Invaded Zone and Mud Cake

Figure 7:
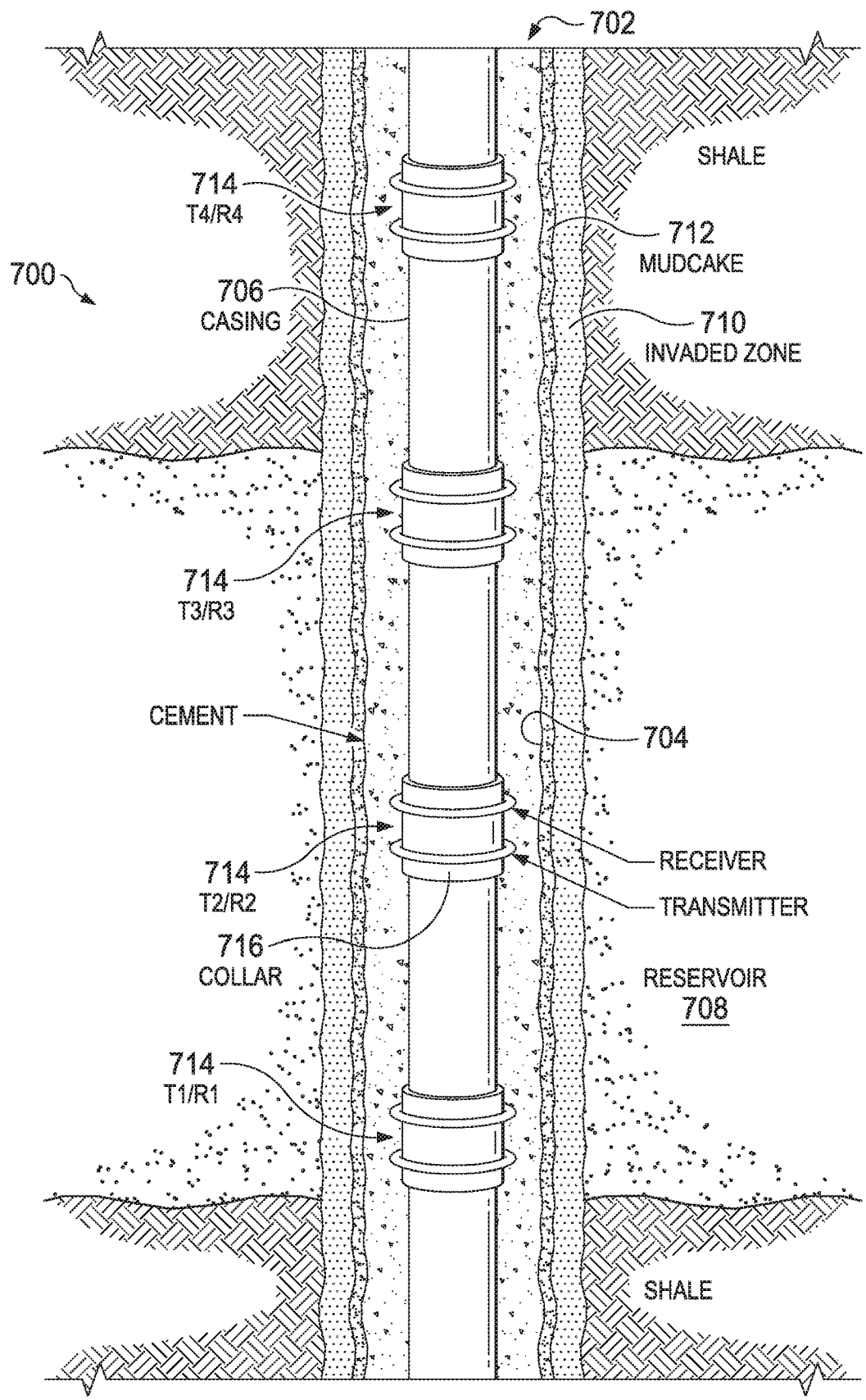
FIG. 7 is a cross-sectional view of an example of a well system that includes a magnetic field sensing system for monitoring invaded zone and mud cake in a wellbore, according to certain embodiments of the present disclosure.

FIG. 7 is a cross-sectional view 700 of an example of a well system that includes a magnetic field sensing system (e.g., an array of transmitters/receivers mounted on casing collars) for monitoring invaded zone and mud cake in a wellbore 702, according to certain illustrative embodiments of the present disclosure. During drilling operation, drilling mud can be injected into an annulus 704 formed between a casing 706 and reservoir formation 708 to assist the drilling process. The drilling mud can be either water-based or oil-based. As illustrated in FIG. 7, the drilling mud filtrate may penetrate into the formation 708, displacing some or all of the formation moveable fluids creating an invaded or a flushed zone 710. Furthermore, the drilling mud residue deposited on wellbore walls can be referred to as a mud cake 712, as further illustrated in FIG. 7. During well completion operation, the mud cake 712 can prevent cement bonding to the formation 708, as shown in FIG. 7. A spacer fluid can be therefore employed before pumping the cement to flush the wellbore and displace the drilling mud.

In one or more embodiments of the present disclosure, the difference in resistivity between the invaded zone 710 (which may also include the mud cake 712) and the formation 708 can be used as an indication of the mobility of formation fluids and for determination of zones where hydrocarbons are recoverable. Given the wellbore (annulus) fluid resistivity (e.g., resistivity of mud/spacer/cement) and the wellbore caliper, the resistivity, width and depth of invasion can be estimated from the shallow (annulus fluid) measurements provided by the disclosed magnetic field sensing system, e.g., by the array of transmitter/receiver pairs 714 mounted on casing collars 716, as illustrated in FIG. 7. For certain embodiments, shallow magnetic field measurements performed by the magnetic field sensing system illustrated in FIG. 7 can be used to detect the presence of residual mud cake 712 (e.g., at least the mud cake adjacent to casing collars) before pumping the cement.

Checking Zonal Isolation by Monitoring Cement Integrity at each Collar

Figure 8A:
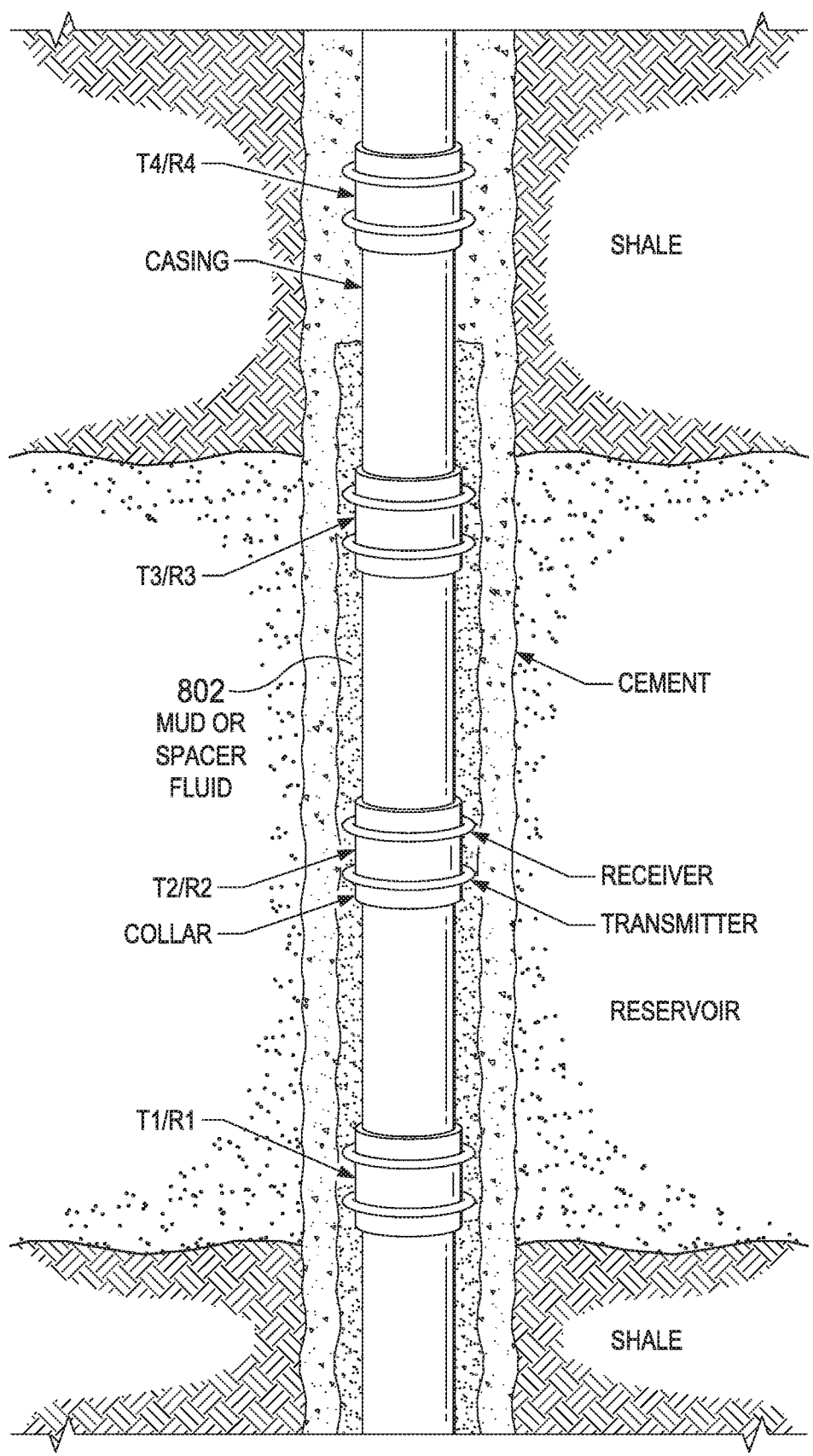
FIG. 8A is a cross-sectional view of an example of a well system that includes a magnetic field sensing system for checking zonal isolation along a casing in a wellbore, which identifies non-isolated zones along the casing, according to certain embodiments of the present disclosure.

In one or more embodiments, residual mud and/or spacer fluid may get trapped between the casing and the cement slurry impairing cement bonding to the casing, and producing zones/pockets of fluids adjacent to the casing. If these zones are extended long enough along the casing, as illustrated in FIG. 8A (e.g., extended non-isolated zones 802), the non-isolated zones may provide conduit for formation fluids to flow adjacent to the casing. This fluid conduit is highly undesirable as it can cause the casing to corrode. Therefore, it is desirable to provide a method and apparatus to check, when improperly cemented zones are present adjacent to the casing, whether these zones are isolated or not. For example, as illustrated in FIG. 8B, zones 804 and 806 are isolated preventing formation fluids to flow adjacent to the casing.

Figure 8B:
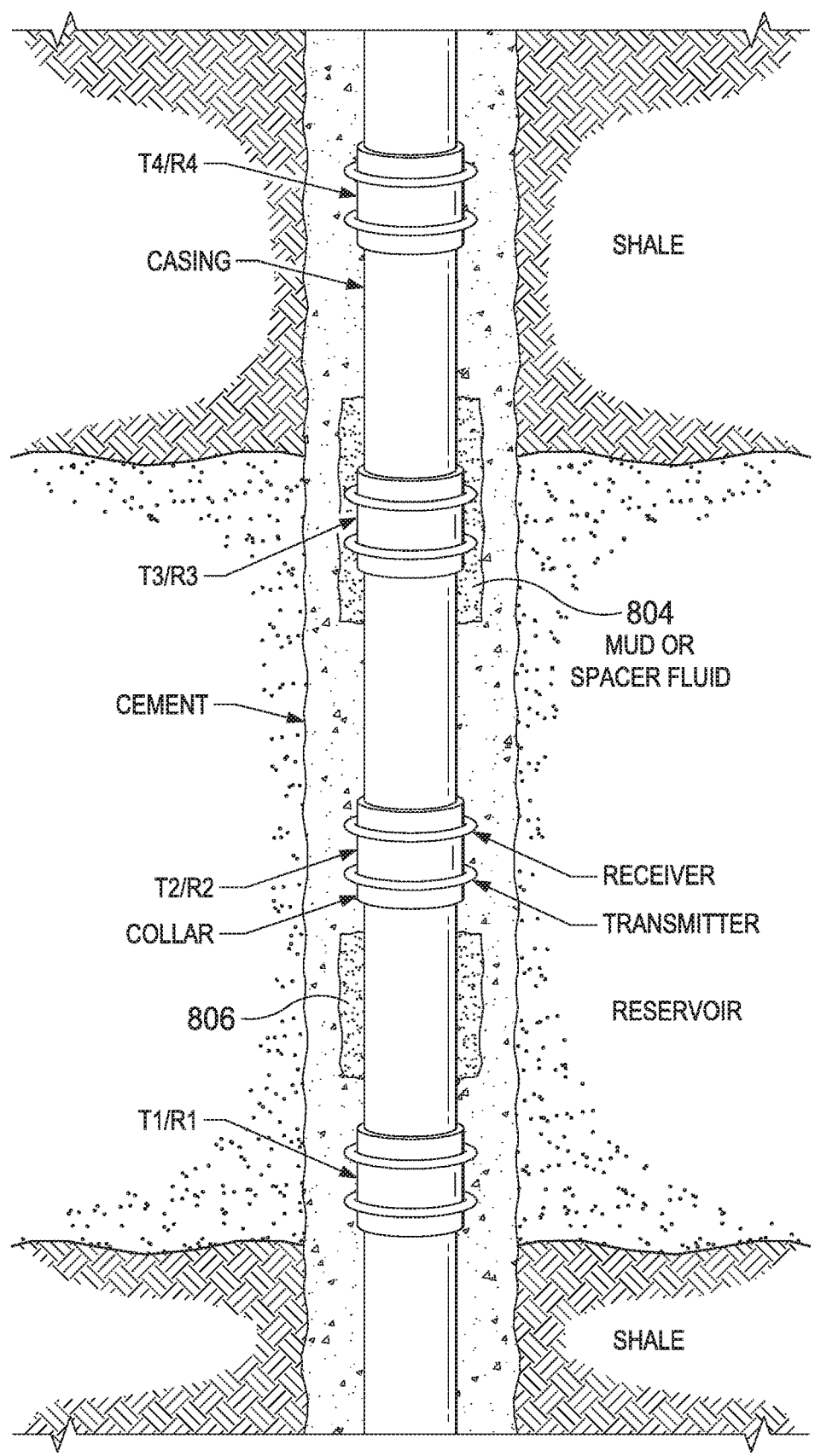
FIG. 8B is a cross-sectional view of an example of a well system that includes a magnetic field sensing system for checking zonal isolation along a casing in a wellbore, which identifies isolated zones along the casing, according to certain embodiments of the present disclosure.

The magnetic field sensing system presented in this disclosure (e.g., an array of transmitter/receiver pairs mounted on casing collars) and illustrated also in FIGS. 8A and 8B can be employed to check zonal isolation through monitoring of the annulus fluid composition at each collar after cement is pumped. In one or more embodiments, a drilling mud or spacer fluids detected at a plurality of consecutive collars (receivers) may indicate a high likelihood of non-isolated zones. As illustrated in FIG. 8A, drilling mud or spacer fluids may be detected at collars of three consecutive receivers R1, R2 and R3, which may indicate a high probability of the extended non-isolated zone 802. In contrast, as illustrated in FIG. 8B, drilling mud or spacer fluids may be detected at collar of receiver R3, whereas cement is detected at collars of receivers R4, R2 and R1. Thus, the improperly cemented zone 804 around receiver R3 is isolated, and formation fluids are prevented to flow adjacent to the casing.

Interrogating RFID Tags Mixed in Cement

For certain embodiments, detection of a top of cement, determining curing state of cement, obtaining characteristics of cement slurry, and the like may be achieved by utilizing RFID tags (or chips). In one or more embodiments, RFID tags can be mixed with the cement slurry pumped into an annulus formed between a casing deployed in a wellbore and formation. An interrogation system can be deployed downhole to detect RFID tags as they pass by. This method provides an alternative approach for monitoring cement besides performing resistivity measurements.

RFID-based interrogation system is an electromagnetic transceiver system. A transmitter (e.g., mounted on a casing) may energize an RFID tag with a narrow band, high frequency electromagnetic field. This electromagnetic field can be received by an antenna connected to the RFID tag, and can power a transponder to return a unique identification "ID" number by modulating and re-radiating a radio frequency (RF) wave. Thus, RFID tags are passive devices that require no battery. For example, commonly used operating bands for RFID systems may center on one of the following assigned frequencies: 125 kHz, 13.56 MHz, 2.45 GHz, or 27.125 MHz.

Figure 9:
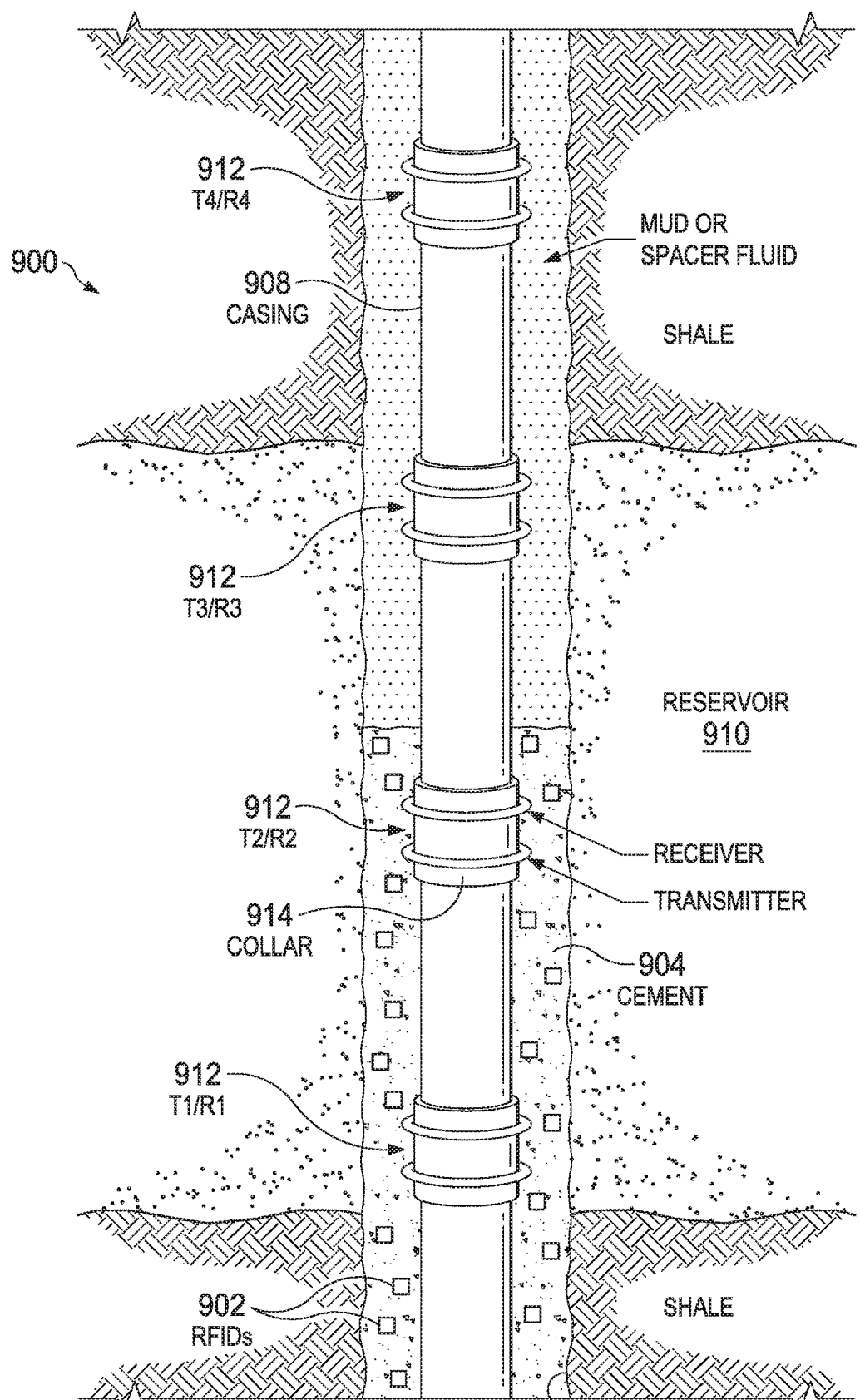
FIG. 9 is a cross-sectional view of an example of a well system that includes a magnetic field sensing system for interrogating radio frequency identification (RFID) tags placed in cement pumped into an annulus in a wellbore between a casing and formation, according to certain embodiments of the present disclosure.

FIG. 9 is a cross-sectional view 900 of an example of a well system that includes the presented magnetic field sensing system (e.g., the array of transmitter/receiver pairs mounted on casing collars) for interrogating RFID tags 902 placed in cement 904 in an annulus 906 between casing 908 and reservoir formation 910, according to certain illustrative embodiments of the present disclosure. In one or more embodiments, the magnetic field sensing system (e.g., the array of transmitter/receiver pairs 912 mounted on casing collars 914) can be used to interrogate the cement-mixed RFID tags 902. The transmitter/receiver pair 912 at each collar 914 may act as a transceiver for RFID interrogation. For certain embodiments, specific RFID interrogation equipment may be deployed downhole. By interrogating the RFID tags 902 placed in the cement 904, information about cement flow in the annulus 906 along the casing 908 may be inferred, and communicated from the receivers 912 to a processing system at a surface.

Figure 10:
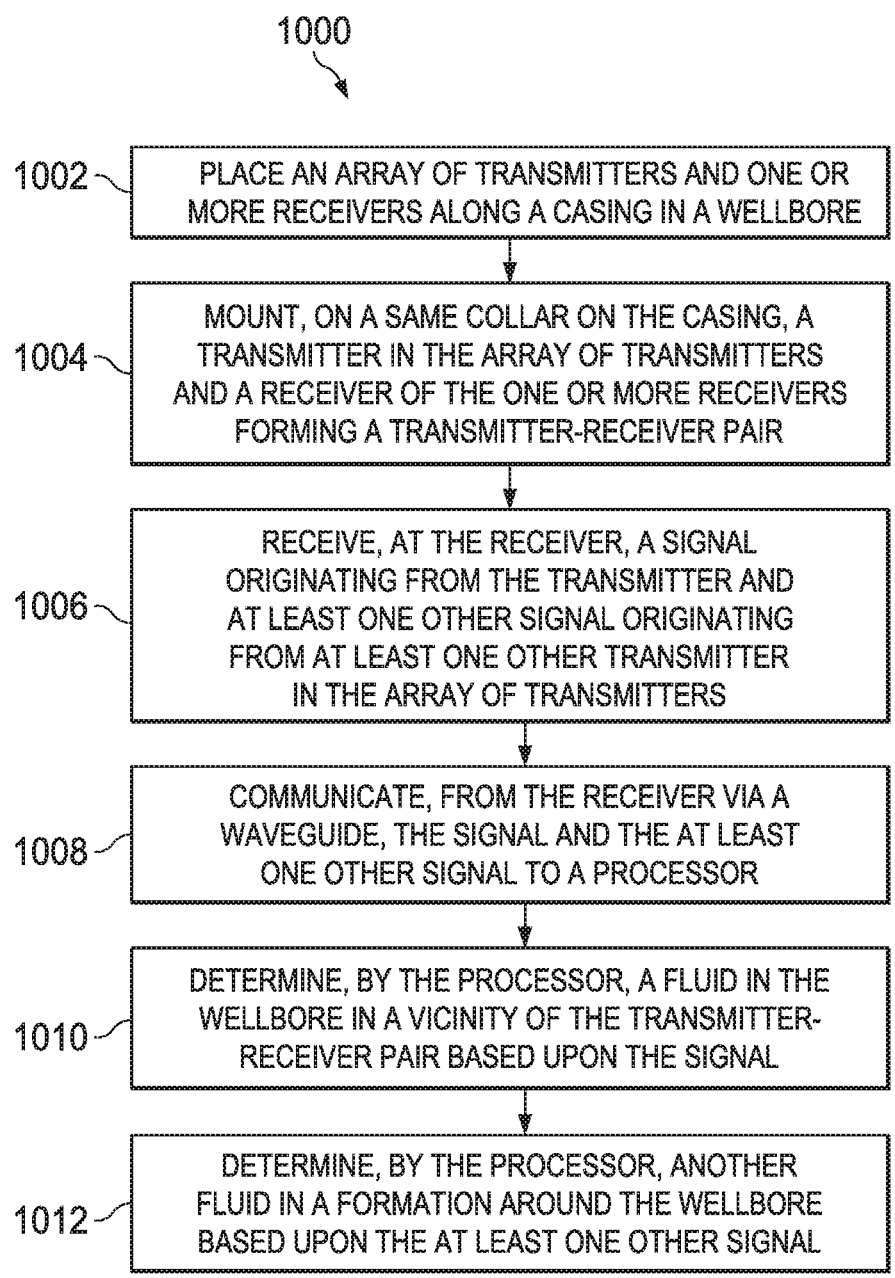
FIG. 10 is a flow chart of a method of electromagnetic sensing for monitoring fluids in a wellbore and/or formation, according to certain embodiments of the present disclosure.

Discussion of an illustrative method of the present disclosure will now be made with reference to FIG. 10, which is a flow chart 1000 of a method of dual-purpose electromagnetic sensing for monitoring wellbore fluids and formation fluids, according to certain illustrative embodiments of the present disclosure. The method begins at 1002 by placing an array of transmitters (e.g., transmitters 106 illustrated in FIG. 1, an array of transmitters 210 from FIG. 2) and one or more receivers (e.g., one or more receivers 106 illustrated in FIG. 1, receiver 212 illustrated in FIG. 2) along a casing (e.g., casing 104 illustrated in FIG. 1, casing 204 illustrated in FIG. 2) in a wellbore (e.g. wellbore 102 illustrated in FIG. 1, wellbore 202 illustrated in FIG. 2). At 1004, a transmitter (e.g., transmitter 210 illustrated in FIG. 2) in the array of transmitters and a receiver (e.g., receiver 212 illustrated in FIG. 2) of the one or more receivers may be mounted on a same collar (e.g., collar 208 illustrated in FIG. 2) on the casing forming a transmitter-receiver pair. At 1006, a signal originating from the transmitter (e.g., transmitter 210 illustrated in FIG. 2) and at least one other signal originating from at least one other transmitter in the array of transmitters (e.g., at least one transmitter 106 illustrated in FIG. 1) may be received at the receiver (e.g., receiver 212 illustrated in FIG. 2). At 1008, the signal and the at least one other signal may be communicated from the receiver to a processor (e.g., an uphole central processing unit, a downhole processor, and/or a computing system 1100 illustrated in FIG. 11) via a waveguide (e.g., signal cable or fiber optic cable 118 illustrated in FIG. 1). At 1010, a fluid in the wellbore in a vicinity of the transmitter-receiver pair (e.g., in annulus 112 illustrated in FIG. 1, in annulus 214 illustrated in FIG. 2) may be determined, by the processor, based upon the signal. At 1012, another fluid in a formation around the wellbore (e.g., formation 114 illustrated in FIG. 1, formation 216 illustrated in FIG. 2) may be determined, by the processor, based upon the at least one other signal.

In one or more embodiments of the present disclosure, the signal received at the receiver (e.g., receiver 212 illustrated in FIG. 2) may originate from the transmitter (e.g., transmitter 210 illustrated in FIG. 2) during a completion stage of a well associated with the wellbore, whereas the at least one other signal received at the receiver (e.g., receiver 212 illustrated in FIG. 2) may originate from the at least one other transmitter (e.g., at least one transmitter 106 illustrated in FIG. 1) during a production stage of the well following the completion stage. For some embodiments, adjustment or optimization of wellbore completion operation, adjustment of well production, and the like may be initiated by the processor (e.g., by computing system 1100 in FIG. 11) based on the determination of the fluid and the determination of the other fluid. For example, in an embodiment, the adjustment or optimization of wellbore completion operation may be initiated by the processor based on the determination of the fluid in the wellbore (fluid in the wellbore being determined based upon the received signal). In another embodiment, the adjustment of well production may be initiated by the processor based on the determination of the other fluid in the formation around the wellbore (the other fluid in the formation being determined based upon the received at least one other signal).

Figure 11:
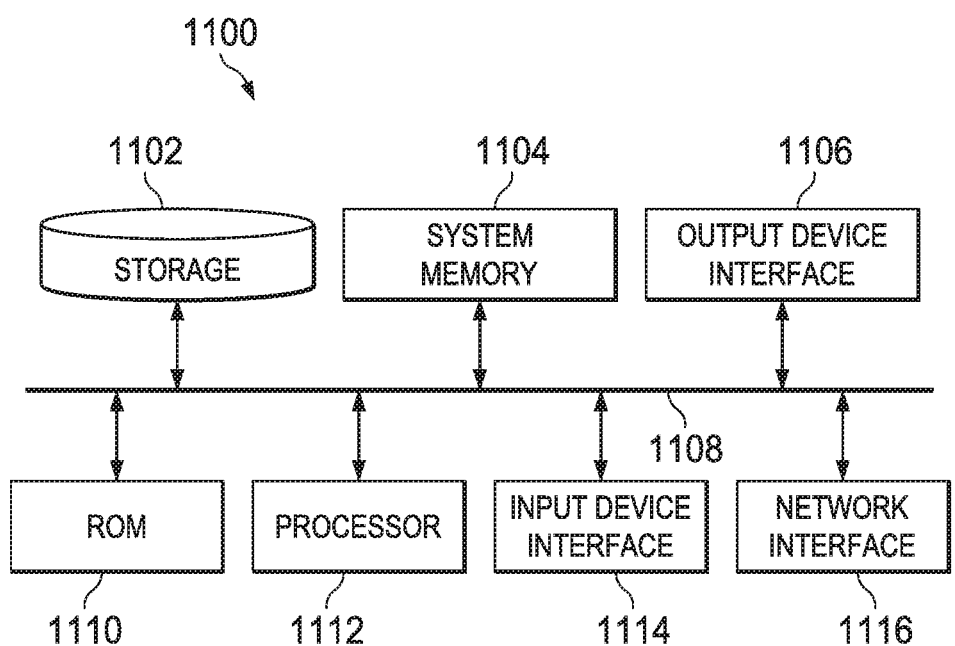
FIG. 11 is a block diagram of an illustrative computer system in which embodiments of the present disclosure may be implemented.

FIG. 11 is a block diagram of an illustrative computing system 1100 in which illustrative embodiments of the present disclosure may be implemented adapted for monitoring fluids in an annulus region formed in a wellbore between a casing and a formation during and after cement is emplaced in the annulus, and for monitoring water floods and other fluid flows from the formation into the wellbore. For example, some of the operations of method 1000 of FIG. 10, as described above, may be implemented using the computing system 1100. The computing system 1100 can be a computer, phone, personal digital assistant (PDA), or any other type of electronic device. Such an electronic device includes various types of computer readable media and interfaces for various other types of computer readable media. The computing system 1100 may be, for example, an integral part of a receiver device of the well system 100 illustrated in FIG. 1 located at a surface (not shown). In one or more embodiments, measurements obtained by the array of transmitter/receiver pairs 106 located along the casing 104 may be telemetered to the receiver device coupled to a central processing unit (e.g., the computing system 1100) at a well head located at a surface (not shown). The computing system 1100 may be configured to receive, from any of the transmitter/receiver pairs 106, measurement data related to locations and characteristics of a fluid located in the annulus 112 in the vicinity of that particular transmitter/receiver pair 106. The computing system 1100 may be further configured to process the received measurement data related to locations and characteristics of fluids in the wellbore 102 and/or fluid flows from the formation 114 to the wellbore 102, provide visual information to a well operator, and initiate appropriate operation(s) related to the wellbore 102 (e.g., certain corrective cementing operations, adjustment of well production, and the like) based on the information about locations and characteristics of fluids along the casing 104 in the wellbore 102 and/or information about water floods and other fluid flows from the formation 114 to the wellbore 102.

As shown in FIG. 11, the computing system 1100 includes a permanent storage device 1102, a system memory 1104, an output device interface 1106, a system communications bus 1108, a read-only memory (ROM) 1110, processing unit(s) 1112, an input device interface 1114, and a network interface 1116.

The bus 1108 collectively represents all system, peripheral, and chipset buses that communicatively connect the numerous internal devices of the computing system 1100. For instance, the bus 1108 communicatively connects the processing unit(s) 1112 with the ROM 1110, the system memory 1104, and the permanent storage device 1102.

From these various memory units, the processing unit(s) 1112 retrieves instructions to execute and data to process in order to execute the processes of the subject disclosure. The processing unit(s) can be a single processor or a multi-core processor in different implementations.

The ROM 1110 stores static data and instructions that are needed by the processing unit(s) 1112 and other modules of the computing system 1100. The permanent storage device 1102, on the other hand, is a read-and-write memory device. This device is a non-volatile memory unit that stores instructions and data even when the computing system 1100 is off. Some implementations of the subject disclosure use a mass-storage device (such as a magnetic or optical disk and its corresponding disk drive) as the permanent storage device 1102.

Other implementations use a removable storage device (such as a floppy disk, flash drive, and its corresponding disk drive) as the permanent storage device 1102. Like the permanent storage device 1102, the system memory 1104 is a read-and-write memory device. However, unlike the storage device 1102, the system memory 1104 is a volatile read-and-write memory, such a random access memory. The system memory 1104 stores some of the instructions and data that the processor needs at runtime. In some implementations, the processes of the subject disclosure are stored in the system memory 1104, the permanent storage device 1102, and/or the ROM 1110. For example, the various memory units include instructions for computer aided pipe string design based on existing string designs in accordance with some implementations. From these various memory units, the processing unit(s) 1112 retrieves instructions to execute and data to process in order to execute the processes of some implementations.

The bus 1108 also connects to the input and output device interfaces 1114 and 1106. The input device interface 1114 enables the user to communicate information and select commands to the computing system 1100. Input devices used with the input device interface 1114 include, for example, alphanumeric, QWERTY, or T9 keyboards, microphones, and pointing devices (also called "cursor control devices"). The output device interfaces 1106 enables, for example, the display of images generated by the computing system 1100. Output devices used with the output device interface 1106 include, for example, printers and display devices, such as cathode ray tubes (CRT) or liquid crystal displays (LCD). Some implementations include devices such as a touchscreen that functions as both input and output devices. It should be appreciated that embodiments of the present disclosure may be implemented using a computer including any of various types of input and output devices for enabling interaction with a user. Such interaction may include feedback to or from the user in different forms of sensory feedback including, but not limited to, visual feedback, auditory feedback, or tactile feedback. Further, input from the user can be received in any form including, but not limited to, acoustic, speech, or tactile input. Additionally, interaction with the user may include transmitting and receiving different types of information, e.g., in the form of documents, to and from the user via the above-described interfaces.

Also, as shown in FIG. 11, the bus 1108 also couples the computing system 1100 to a public or private network (not shown) or combination of networks through a network interface 1116. Such a network may include, for example, a local area network ("LAN"), such as an Intranet, or a wide area network ("WAN"), such as the Internet. Any or all components of the computing system 1100 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself. Accordingly, some of the operations of method 1000 of FIG. 10, as described above, may be implemented using the computing system 1100 of FIG. 11 or any computer system having processing circuitry or a computer program product including instructions stored therein, which, when executed by at least one processor, causes the processor to perform functions relating to these methods.

As used in this specification and any claims of this application, the terms "computer", "server", "processor", and "memory" all refer to electronic or other technological devices. These terms exclude people or groups of people. As used herein, the terms "computer readable medium" and "computer readable media" refer generally to tangible, physical, and non-transitory electronic storage mediums that store information in a form that is readable by a computer.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs implemented on the respective computers and having a client-server relationship to each other. In some embodiments, a server transmits data (e.g., a web page) to a client device (e.g., for purposes of displaying data to and receiving user input from a user interacting with the client device). Data generated at the client device (e.g., a result of the user interaction) can be received from the client device at the server.

It is understood that any specific order or hierarchy of operations in the processes disclosed is an illustration of exemplary approaches. Based upon design preferences, it is understood that the specific order or hierarchy of operations in the processes may be rearranged, or that all illustrated operations be performed. Some of the operations may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Furthermore, the illustrative methods described herein may be implemented by a system including processing circuitry or a computer program product including instructions which, when executed by at least one processor, causes the processor to perform any of the methods described herein.

A method for dual-purpose electromagnetic sensing to monitor wellbore fluids and formation fluids has been described and may generally include: placing an array of transmitters and one or more receivers along a casing in a wellbore; mounting, on a same collar on the casing, a transmitter in the array of transmitters and a receiver of the one or more receivers forming a transmitter-receiver pair; receiving, at the receiver, a signal originating from the transmitter and at least one other signal originating from at least one other transmitter in the array of transmitters; communicating, from the receiver via a waveguide, the signal and the at least one other signal to a processor; determining, by the processor, a fluid in the wellbore in a vicinity of the transmitter-receiver pair based upon the signal; and determining, by the processor, another fluid in a formation around the wellbore based upon the at least one other signal.

For the foregoing embodiments, the method may include any one of the following operations, alone or in combination with each other: Generating signals for a plurality of transmitters in the array of transmitters having a range of frequencies by a power generator interfaced with an electric power cable connected to the plurality of transmitters; Receiving, at the receiver, the signal originating from the transmitter of the transmitter-receiver pair before and after a cement is pumped into an annulus between the casing and the formation; Monitoring curing process of the cement based on the received signal; Receiving, at the receiver, the signal originating from the transmitter of the transmitter-receiver pair as a cement is pumped into an annulus between the casing and the formation replacing at least one of a drilling mud or a spacer fluid in the annulus; Monitoring a top of the cement based on the received signal; Receiving, at the receiver, the signal originating from the transmitter of the transmitter-receiver pair after a cement is pumped into an annulus between the casing and the formation replacing a spacer fluid used to flush a drilling mud in the annulus; Determining, based on the received signal, a width of an invaded zone where the drilling mud invaded the formation; Determining, based on the received signal, whether a residual of the drilling mud is deposited on a wall of the wellbore; Receiving, at the receiver, the signal originating from the transmitter of the transmitter-receiver pair after a cement slurry is pumped into an annulus between the casing and the formation replacing a spacer fluid used to flush a drilling mud in the annulus; Determining, based on the received signal, whether a residual of the spacer fluid or a residual of the drilling mud is located between the casing and the cement slurry in a vicinity of the receiver; Interrogating, by the array of transmitters and the one or more receivers, one or more RFID tags mixed in a cement slurry pumped into an annulus between the casing and the formation to obtain one or more received signals; Determining characteristics of the cement slurry based on the one or more received signals; Determining, based upon the signal received at the receiver, a resistivity of the fluid located around the receiver in an annulus between the casing and the formation; Determining, based upon the at least one other signal received at the receiver, a resistivity of the other fluid in the formation around the wellbore; Initiating, by the processor, optimization of completion operation of the wellbore based on the determination of the fluid.

The waveguide comprises a fiber optic cable interfaced with the receiver; The signal originates from the transmitter during a completion stage of the wellbore, and the at least one other signal originates from the at least one other transmitter during a production stage of the wellbore following the completion stage.

Likewise, a dual-purpose electromagnetic sensing system for monitoring wellbore fluids and formation fluids has been described and includes: an array of transmitters and one or more receivers located along a casing in a wellbore, wherein a transmitter in the array of transmitters and a receiver of the one or more receivers are mounted on a same collar on the casing forming a transmitter-receiver pair, the receiver receives a signal originating from the transmitter and at least one other signal originating from at least one other transmitter in the array of transmitters, the signal being indicative of a fluid in the wellbore in a vicinity of the transmitter-receiver pair and the at least one other signal being indicative of another fluid in a formation around the wellbore, and the receiver communicates, via a waveguide, the signal and the at least one other signal to a processor.

For any of the foregoing embodiments, the system may include any one of the following elements, alone or in combination with each other: another transmitter of the array of transmitters and another receiver of the one or more receivers forming another transmitter-receiver pair are mounted on a different collar on the casing; transmitters in the array of transmitters comprise an array of coils mounted on the casing, connected in series, and fed by an electric power cable; a power generator interfaced to the electric power cable configured to generate signals for the transmitters having a range of frequencies; the receiver comprises a coil mounted on the casing, connected to the waveguide; the waveguide comprises a fiber optic cable interfaced with the receiver; the processor is configured to acquire and process the signal and the at least one other signal communicated from the receiver by the waveguide; the processor is configured to initiate one or more operations related to the wellbore based on the processed signals; the processor is located at a surface; the processor is a downhole processor.

The signal and the at least one other signal received at the receiver are indicative of resistivity of the fluid in the wellbore and resistivity of the other fluid in the formation; The signal received at the receiver is indicative of at least one of: a top of a cement pumped into an annulus between the casing and the formation replacing a spacer fluid used to flush a drilling mud in the annulus, curing state of the cement, a width of an invaded zone where the drilling mud invaded the formation, a residual of the drilling mud deposited on a wall of the wellbore, or a residual of the spacer fluid or a residual of the drilling mud located between the casing and the cement.

Likewise, a dual-purpose electromagnetic sensing tool for monitoring wellbore fluids and formation fluids has been described and includes: an array of transmitters and one or more receivers adapted to be located along a casing in a wellbore; and a receiver of the one or more receivers forming a transmitter-receiver pair with a transmitter in the array adapted to receive a signal originating from the transmitter and at least one other signal originating from at least one other transmitter in the array, the signal being indicative of a fluid in the wellbore in a vicinity of the transmitter-receiver pair and the at least one other signal being indicative of another fluid in a formation around the wellbore. The signal and the at least one other signal received at the receiver of the tool are indicative of resistivity of the fluid in the wellbore and resistivity of the other fluid in the formation.

Embodiments of the present disclosure are related to the dual-purpose electromagnetic sensing system for monitoring fluids in a wellbore and water floods and other fluids in a formation around the wellbore, and may be permanently deployed along a casing string in the wellbore. An array of magnetic field transmitters and receivers of the dual-purpose electromagnetic sensing system implemented in this disclosure can support interventionless monitoring of fluids in the wellbore and the formation. Embodiments of the present disclosure further allow two-dimensional (2D) mapping for depths of interest.

The method and apparatus presented in this disclosure can identify, discriminate, and monitor fluids (e.g., cement, spacer fluid, and drilling mud) present in an annulus formed in the wellbore between the casing and the formation. The method and apparatus presented herein can further monitor the cure state of cement pumped into the annulus between the casing and formation. Embodiments of the present disclosure can also support monitoring cement health during life-of-well, e.g., degradation from $CO_2$ exposure. Embodiments of the present disclosure can be deployed in onshore wells, as well as to offshore wells.

Embodiments of the present disclosure support efficient and low-cost pre-fabrication and calibration. The electromagnetic sensing system presented herein can be realized with highly reliable materials, which can maintain integrity and performance in high pressure environments such as those typically encountered downhole, particularly in high pressure, high temperature (HPHT) deepwater wells.

Embodiments of the present disclosure can support time-lapse electromagnetic modeling, inversion, and/or imaging for monitoring fluid displacements in a wellbore and a formation. The multi-purpose electromagnetic sensing system presented herein can be interfaced with integrated well management software and related workflows through, for example, an application programmable interface (API). Embodiments of the present disclosure can further support decision making in order to facilitate well management.

In general, embodiments of the present disclosure relate to electromagnetic based fluid sensing technology and applications. Embodiments of the present disclosure further relate to extension of a permanent monitoring system to include cement monitoring and waterflood monitoring.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

While specific details about the above embodiments have been described, the above hardware and software descriptions are intended merely as example embodiments and are not intended to limit the structure or implementation of the disclosed embodiments. For instance, although many other internal components of computer system 1100 illustrated in FIG. 11 are not shown, those of ordinary skill in the art will appreciate that such components and their interconnection are well known.

In addition, certain aspects of the disclosed embodiments, as outlined above, may be embodied in software that is executed using one or more processing units/components. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives, optical or magnetic disks, and the like, which may provide storage at any time for the software programming.

Additionally, the flowchart and block diagrams in the figures illustrate the architecture, functionality, and operation of possible implementations of systems, methods and computer program products according to various embodiments of the present disclosure. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The above specific example embodiments are not intended to limit the scope of the claims. The example embodiments may be modified by including, excluding, or combining one or more features or functions described in the disclosure.

What is claimed is:

1. A dual-purpose electromagnetic sensing system for monitoring wellbore fluids and formation fluids, the system comprising:
    an array of transmitters and one or more receivers located along a casing in a wellbore, wherein:
    a transmitter in the array of transmitters and a receiver of the one or more receivers are coils mounted on a same ferrite sleeve that is positioned over a same collar that is positioned on and around the casing, thereby forming a transmitter-receiver pair,
    the receiver receives a signal originating from the transmitter and at least one other signal originating from at least one other transmitter in the array of transmitters, and
    the receiver communicates, via a waveguide, the signal and the at least one other signal to a processor, wherein the signal is used to identify a type of fluid in the wellbore in a vicinity of the transmitter-receiver pair and the at least one other signal is used to identify a type of another fluid in a formation around the wellbore.

2. The system of claim 1, wherein another transmitter of the array of transmitters and another receiver of the one or more receivers forming another transmitter-receiver pair are mounted on a different collar on the casing.

3. The system of claim 1, wherein the signal and the at least one other signal received at the receiver are indicative of resistivity of the fluid in the wellbore and resistivity of the other fluid in the formation.

4. The system of claim 1, wherein the signal received at the receiver is indicative of at least one of:
    a top of a cement pumped into an annulus between the casing and the formation replacing a spacer fluid used to flush a drilling mud in the annulus,
    curing state of the cement,
    a width of an invaded zone where the drilling mud invaded the formation,
    a residual of the drilling mud deposited on a wall of the wellbore, or
    a residual of the spacer fluid or a residual of the drilling mud located between the casing and the cement.

5. The system of claim 1, wherein transmitters in the array of transmitters comprise an array of coils mounted on the casing, connected in series, and fed by an electric power cable.

6. The system of claim 5, further comprising a power generator interfaced to the electric power cable configured to generate signals for the transmitters having a range of frequencies.

7. The system of claim 1, wherein the receiver comprises a coil mounted on the casing, connected to the waveguide.

8. The system of claim 1, wherein the waveguide comprises a fiber optic cable interfaced with the receiver.

9. The system of claim 1, wherein:
    the processor is configured to acquire and process the signal and the at least one other signal communicated from the receiver by the waveguide, and
    the processor is further configured to initiate one or more operations related to the wellbore based on the processed signals.

10. The system of claim 1, wherein the processor is located at a surface.

11. The system of claim 1, wherein the processor is a downhole processor.

12. The system of claim 1, wherein the signal originates from the transmitter during a completion stage of the wellbore, and the at least one other signal originates from the at least one other transmitter during a production stage of the wellbore following the completion stage.

13. A method for dual-purpose electromagnetic sensing to monitor wellbore fluids and formation fluids, the method comprising:
    placing an array of transmitters and one or more receivers along a casing in a wellbore;
    mounting, on a same ferrite sleeve that is positioned over a same collar that is positioned on and around the casing, a transmitter in the array of transmitters and a receiver of the one or more receivers forming a transmitter-receiver pair, wherein the transmitter and the receiver are coils;
    receiving, at the receiver, a signal originating from the transmitter and at least one other signal originating from at least one other transmitter in the array of transmitters;
    communicating, from the receiver via a waveguide, the signal and the at least one other signal to a processor;
    identifying, by the processor, a type of fluid in the wellbore in a vicinity of the transmitter-receiver pair based upon the signal; and
    identifying, by the processor, a type of another fluid in a formation around the wellbore based upon the at least one other signal.

14. The method of claim 13, further comprising generating signals for a plurality of transmitters in the array of transmitters having a range of frequencies by a power generator interfaced with an electric power cable connected to the plurality of transmitters.

15. The method of claim 13, wherein the waveguide comprises a fiber optic cable interfaced with the receiver.

16. The method of claim 13, further comprising:
    receiving, at the receiver, the signal originating from the transmitter of the transmitter-receiver pair before and after a cement is pumped into an annulus between the casing and the formation; and
    monitoring a cure state of the cement based on the signal received at the receiver.

17. The method of claim 13, further comprising:
receiving, at the receiver, the signal originating from the transmitter of the transmitter-receiver pair as a cement is pumped into an annulus between the casing and the formation replacing at least one of a drilling mud or a spacer fluid in the annulus; and
monitoring a location of a top of the cement based on the signal received at the receiver.

18. The method of claim 13, further comprising:
receiving, at the receiver, the signal originating from the transmitter of the transmitter-receiver pair after a cement is pumped into an annulus between the casing and the formation replacing a spacer fluid used to flush a drilling mud in the annulus;
determining, based on the signal received at the receiver, a width of an invaded zone where the drilling mud invaded the formation; and
determining, based on the signal, whether a residual of the drilling mud is deposited on a wall of the wellbore.

19. The method of claim 13, further comprising:
receiving, at the receiver, the signal originating from the transmitter of the transmitter-receiver pair after a cement slurry is pumped into an annulus between the casing and the formation replacing a spacer fluid used to flush a drilling mud in the annulus; and
determining, based on the signal received at the receiver, whether a residual of the spacer fluid or a residual of the drilling mud is located between the casing and the cement slurry in a vicinity of the receiver.

20. The method of claim 13, further comprising:
interrogating, by the array of transmitters and the one or more receivers, one or more radio frequency identification (RFID) tags mixed in a cement slurry pumped into an annulus between the casing and the formation to obtain one or more received signals; and
determining characteristics of the cement slurry based on the one or more received signals.

21. The method of claim 13, wherein the identification by the processor comprises:
determining, based upon the signal received at the receiver, a resistivity of the fluid located around the receiver in an annulus between the casing and the formation.

22. The method of claim 13, wherein the identification by the processor comprises:
determining, based upon the at least one other signal received at the receiver, a resistivity of the other fluid in the formation around the wellbore.

23. The method of claim 13, further comprising initiating, by the processor, optimization of completion operation of the wellbore based on the identification of the fluid.

24. The method of claim 13, wherein the signal originates from the transmitter during a completion stage of the wellbore, and the at least one other signal originates from the at least one other transmitter during a production stage of the wellbore following the completion stage.

25. A dual-purpose electromagnetic sensing tool for monitoring wellbore fluids and formation fluids, comprising:
an array of transmitters and one or more receivers adapted to be located along a casing in a wellbore; and
a receiver of the one or more receivers forming a transmitter-receiver pair with a transmitter in the array adapted to receive a signal originating from the transmitter and at least one other signal originating from at least one other transmitter in the array, the signal being used to identify a type of fluid in the wellbore in a vicinity of the transmitter-receiver pair and the at least one other signal being used to identify a type of another fluid in a formation around the wellbore,
wherein the receiver and the transmitter are coils mounted on a same ferrite sleeve that is positioned over a same collar that is positioned on and around the casing.

26. The tool of claim 25, wherein the signal and the at least one other signal received at the receiver of the tool are indicative of resistivity of the fluid in the wellbore and resistivity of the other fluid in the formation.

* * * * *